US008669093B2

(12) United States Patent
Wade et al.

(10) Patent No.: US 8,669,093 B2
(45) Date of Patent: Mar. 11, 2014

(54) BIOCATALYST FOR PRODUCTION OF D-LACTIC ACID

(75) Inventors: Mitsufumi Wade, Mobara (JP); Toshihiro Oikawa, Mobara (JP); Daisuke Mochizuki, Mobara (JP); Junko Tokuda, Mobara (JP); Miyuki Kawashima, Mobara (JP); Tadashi Araki, Mobara (JP); Reiko Abe, Mobara (JP); Hitoki Miyake, Mobara (JP); Hitoshi Takahashi, Mobara (JP); Hideki Sawai, Kamakura (JP); Takashi Mimitsuka, Kamakura (JP); Takashi Morishige, Mobara (JP); Yosuke Higashi, Mobara (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 1196 days.

(21) Appl. No.: 10/573,813

(22) PCT Filed: Sep. 17, 2004

(86) PCT No.: PCT/JP2004/014037
§ 371 (c)(1),
(2), (4) Date: Jul. 27, 2006

(87) PCT Pub. No.: WO2005/033324
PCT Pub. Date: Apr. 14, 2005

(65) Prior Publication Data
US 2007/0065930 A1    Mar. 22, 2007

(30) Foreign Application Priority Data

Sep. 30, 2003 (JP) ................. 2003-340062
Sep. 30, 2003 (JP) ................. 2003-342165
Sep. 30, 2003 (JP) ................. 2003-342222
May 20, 2004 (JP) ................. 2004-150252
May 20, 2004 (JP) ................. 2004-150253

(51) Int. Cl.
*C12N 1/21* (2006.01)
*C12P 7/56* (2006.01)
*C12N 1/26* (2006.01)

(52) U.S. Cl.
USPC ...... 435/252.33; 435/139; 435/170; 536/23.7

(58) Field of Classification Search
USPC ............... 435/252.33, 139, 170; 536/23.7
See application file for complete search history.

(56) References Cited

U.S. PATENT DOCUMENTS 8,426,191 B2 * 4/2013 Zhou et al. ............ 435/252.33
2006/0148041 A1 * 7/2006 Maier .................... 435/106

FOREIGN PATENT DOCUMENTS

JP    11-056361 A    3/1999
JP    2003-159091 A    6/2003

OTHER PUBLICATIONS

Nielsen Metabolic engineering Applied Microbiology and Biotechnology, 2001 55:263-283.*
Zhou et al., "Production of Optically Pure D-Lactic Acid in Mineral Salts Medium by Metabolically Engineered *Escherichia coli* W3110," *Applied and Environmental Microbiology*, Jan. 2003, pp. 399-407, vol. 69, No. 1, American Society of Microbiology.
Dym et al., "The crystal structure of D-lactate dehydrogenase, a peripheral membrane respiratory enzyme," *Proc. Natl. Acad. Sci.*, Aug. 15, 2000, pp. 9413-9418, vol. 97, No. 17, USA.
Blattner et al., "*Escherichia coli* K-12 MG1655 section 192 of 400 of the complete genome," Database GenBank Accession No. AE000302, Dec. 1, 2000.
Shaw et al., "Vinylglycolate Resistance in *Escherichia coli*," *Journal of Bacteriology*, Mar. 1975, pp. 1047-1055, vol. 121, No. 3, American Society for Microbiology.
Mochizuki et al., "Test Production of D-lactic Acid by Use of *Bacillus coli*," Presentation at the Japan Agricultural and Horticultural Chemistry Society 2004 Convention, Mar. 2004, No. 2A11p22, p. 43, Japan Society for Bioscience, Biotechnology and Agrochemistry.
Chang et al., Homofermentative Production of D- or L-Lactate in Metabolically Engineered *Escherichia coli* RR1, *Applied and Environmental Microbiology*, Apr. 1999, pp. 1384-1389, vol. 65, No. 4, American Society for Microbiology.
Contag et al., "Cloning of a Lactate Dehydrogenase Gene from *Clostridium acetobutylicum* B643 and Expression in *Escherichia coli*," *Applied and Environmental Microbiology*, Dec. 1990, pp. 3760-3765, vol. 56, No. 12, American Society for Microbiology.
Yang et al., "Redistribution of Metabolic Fluxes in *Escherichia coli* with Fermentative Lactate Dehydrogenase Overexpression and Deletion," *Metabolic Engineering* 1, 1999, pp. 141-152, Academic Press.
Bunch et al., "The *IdhA* gene encoding the fermentative lactate dehydrogenase of *Escherichia coli*," *Microbiology*, 1997, pp. 187-195, vol. 143, Great Britain.

(Continued)

*Primary Examiner* — Maria Leavitt
(74) *Attorney, Agent, or Firm* — Buchanan Ingersoll & Rooney PC

(57) ABSTRACT

A method for producing D-lactic acid in high yield, and to provide a method for producing D-lactic acid with high selectivity, in which optical purity is high and a by-product organic acid is small. In one aspect, a microorganism, wherein activity of pyruvate formate-lyase (pfl) is inactivated or decreased, and further activity of *Escherichia coli*-derived NADH-dependent D-lactate dehydrogenase (ldhA) is enhanced, is cultured to efficiently produce D-lactic acid. With regard to a method for enhancing ldhA activity, by linking, on a genome, a gene encoding ldhA with a promoter of a gene which controls expression of a protein involved in a glycolytic pathway, a nucleic acid biosynthesis pathway or an amino acid biosynthesis pathway, suitable results are obtained compared to the method for enhancing expression of the gene using an expression vector. A microorganism in which a dld gene is substantially inactivated or decreased is cultured to produce high quality D-lactic acid with reduced concentration of pyruvic acid.

18 Claims, 3 Drawing Sheets

(56) References Cited

OTHER PUBLICATIONS

Kochhar et al., "Cloning and overexpression of *Lactobacillus helveticus* D-lactate dehydrogenase gene in *Escherichia coli*," *Eur. J. Biochem.*, 1992, pp. 799-805, vol. 308, FEBS.

Kochhar et al., "Cloning and overexpression of the *Lactobacillus bulgaricus* NAD+-dependent D-lactate dehydrogenase gene in *Escherichia coli*: purification and characterization of the recombinant enzyme," *Biochemical and Biophysical Research Communications*, Jun. 15, 1992, pp. 705-712, vol. 185, No. 2, Academic Press, Inc.

Solem et al., "Modulation of Gene Expression Made Easy," *Applied and Environmental Microbiology*, May 2002, pp. 2397-2403, vol. 68, No. 5, American Society for Microbiology.

Barnes et al., "Mechanisms of Active Transport in Isolated Membrane Vesicles," *The Journal of Biological Chemistry*, Sep. 10, 1971, pp. 5518-5522, vol. 246, No. 17, USA.

Mat-Jan et al., "Mutants of *Escherichia coli* Deficient in the Fermentative Lactate Dehydrogenase," *Journal of Bacteriology*, Jan. 1989, pp. 342-348, vol. 171, No. 1, American Society for Microbiology.

Courtright et al., "Malate Dehydrogenase Mutants in *Escherichia coli* K-12," *Journal of Bacteriology*, Jun. 1970, pp. 722-728, vol. 102, No. 3, American Society for Microbiology.

Dreyfus et al., "Consequences of Aspartase Deficiency in *Yersinia pestis*," *Journal of Bacteriology*, Nov. 1978, pp. 757-764, vol. 136, No. 2, American Society for Microbiology.

Hansen et al., "Properties of Mutants of *Escherichia coli* Lacking Malic Dehydrogenase and Their Revertants," *The Journal of Biological Chemistry*, May 10, 1979, pp. 3570-3575, vol. 254, No. 9.

Supplemental European Search Report for Application No. 04773417.3-1521/1669460 mailed May 13, 2011.

BS Dien et al., *Recombinant Escherichia coli engineered for production of L-lactic acid from hexose and penose sugars*, 27 Journal of Industrial Microbiology & Biotechnology 259-264 (2001).

J. Zhu et al., *The effect of pfl gene knockout on the metabolism for optically pure D-lactate production by Escherichia coli*, 64 Appl Microbiol Biotechnol 367-375 (2004).

* cited by examiner

– 1 –

BIOCATALYST FOR PRODUCTION OF D-LACTIC ACID

TECHNICAL FIELD

The present invention relates to a microorganism which produces D-lactic acid in high yield with high selectivity, and a method for producing D-lactic acid using it. Specifically, it relates to a method for producing lactic acid with high purity in good efficiency, especially a method for efficiently producing D-lactic acid in which an amount of pyruvic acid produced and accumulated is small.

In addition, the present invention relates to a method for producing D-lactic acid, wherein the method is characterized by using a microorganism in which FAD-dependent D-lactate dehydrogenase is inactivated or decreased.

In addition, the present invention relates to a microorganism producing D-lactic acid without producing succinic acid and fumaric acid that are impurities, and a method for producing D-lactic acid using it.

BACKGROUND ART

Polylactic acid, which is a biodegradable polymer, draws strong attention as a product responding to sustainability and LCA (life cycle assessment) with actualization of $CO_2$ problem and energy problem, and an efficient and economical production method is required for lactic acid, which is a raw material thereof.

Incidentally, polylactic acid produced industrially currently is an L-lactic acid polymer. However, lactic acid includes L-lactic acid and D-lactic acid. D-lactic acid is calling attention in recent years as a raw material for polymers or intermediates of agricultural chemicals and medicines. However, lactic acid as a raw material is required to have high optical purity for any use.

In the nature, there exists a microorganism which produces lactic acid in good efficiency such as *lactobacillus* and filamentous bacteria, and some of methods for producing lactic acid using them have already come into practical use. For example, *Lactbacillus delbrueckii* or the like is known as a microorganism producing L-lactic acid in good efficiency, and microorganisms belonging to the genus *Sporolactobacillus* or the like as microorganisms producing D-lactic acid in good efficiency. In all cases, the amount of lactic acid accumulated reaches high level, but by-products contained in the culture solution other than lactic acid, for example, compounds such as acetic acid, ethanol, acetoin and pyruvic acid, which are not removed in the purification process, may lead to decrease in the quality of lactic acid, which is the final product. In addition, it is also a critical problem that contamination due to optical isomers can cause decrease in optical purity.

To avoid such decrease in the purity of lactic acid, it is an effective means to decrease the amount of by-products produced by a microorganism. It has become possible to inhibit specifically production of the aimed by-products by disruption of a certain gene of a microorganism using a gene recombination technique which has been developed in recent years. However, it does not mean that the gene disruption method can be easily applied to any microorganism in reality, and it is not easy to apply it to a microorganism which can originally produce lactic acid in high yield such as *lactobacillus* or filamentous bacteria or the like. It is because genome information of these microorganisms cannot always be known sufficiently, and further they are not universally used as a host of gene recombination.

In contrast, it is possible to perform gene disruption relatively easily for *Escherichia coli*, yeast, human culture cell or the like, for which genome information is abundant, and which have sufficient records as a host of gene recombination. Especially, *Escherichia coli* is most preferred in view of growth rate or easiness of culturing. Furthermore, since *Escherichia coli* produces only D-isomer of lactic acid, it is a suitable host for the purpose of obtaining D-lactic acid with high optical purity. However, wild type of *Escherichia coli* has low productivity for D-lactic acid, and produces a variety of by-product organic acids in addition to D-lactic acid. To solve this problem, it has been tried in the past to modify metabolic pathway of *Escherichia coli* by gene recombination, for selectively producing D-lactic acid in high yield.

Chang, et al. (Chang, D.-E., et. al., Appl. Environ. Microbiol., Vol. 65(4), pp 1384-1389 (1999)) were able to produce 62.2 g/L of D-lactic acid in 60 hours, by culturing a double variant of phosphotransacetylase (hereinafter, may be simply referred to as pta) and phosphoenolpyruvic carboxylase (hereinafter, may be simply referred to as ppc) of *Escherichia coli* using a medium containing 5% glucose and amino acids and after increasing the amount of microbial mass by preliminary culturing under aeration, culturing was performed under anaerobic conditions, and by further culturing and adding glucose to the medium so as to maintain glucose concentration at 5% or less in the medium. In this case, the conversion rate from glucose to D-lactic acid was 76%.

Zhou, et al. (Zhou, S., et. al., Appl. Environ. Microbiol., Vol. 69(1), pp 399-407 (2003)) reported that *Escherichia coli* quadruply disrupted in pyruvate formate-lyase (hereinafter, may be simply referred to as pfl), fumarate reductase (hereinafter, may be simply referred to as frd), alcohol/aldehyde dehydrogenase (hereinafter, may be simply referred to as adeE) and acetate kinase (hereinafter, may be simply referred to as ackA) was prepared and cultured in an inorganic salt medium containing 5% glucose under anaerobic conditions for 168 hours to produce 48.5 g/L of D-lactic acid with no by-product of formic acid, succinic acid, ethanol and acetic acid. However, this attempt cannot be said to satisfy both of selection rate and productivity because of low productivity such as 0.29 g/L/hr although it was successful for producing D-lactic acid with high selectivity. In addition, there is no mention about by-product pyruvic acid, and effects of its decrease are unclear. Since pyruvic acid is a metabolic reaction substrate of D-lactic acid, it is different from other by-product organic acids, and if its production is suppressed thoughtlessly, production of D-lactic acid itself is suppressed as well. In that point, it is not easy to suppress by-production of pyruvic acid to a minimum. Generally, it is a well-known fact to a person skilled in the art that when pyruvic acid is contained as an impurity in a raw material for lactic acid monomer, unwanted problems occur such as decrease in polymer polymerization rate or the like. For this reason as well, pyruvic acid is one of by-products that should be decreased by all means. However, there has been no report in the past that by-production of pyruvic acid is suppressed while maintaining high productivity of D-lactic acid successfully.

In summary, the maximum amount of D-lactic acid accumulated with *Escherichia coli* known until now has been 62.2 g/L with the production time of 60 hours. On the other hand, if it is considered that L-lactic acid productivity of *lactobacillus* or filamentous bacteria, which is used in industrial production of L-lactic acid, is not less than 100 g/L in the amount accumulated and further the production time is within 24 hours, it would have to be said that the amount of D-lactic acid accumulated and the production time in the case of

*Escherichia coli* are still at low level. There was no report in the past that *Escherichia coli* achieved lactic acid productivity as much as that of *lactobacillus* or filamentous bacteria, and far from it, there was no data in the past which suggest whether or not D-lactic acid can be accumulated and produced exceeding 100 g/L using *Escherichia coli*.

When D-lactic acid is fermented using *Escherichia coli*, the presence of oxygen is generally considered not to be preferable. It is because, if an electron acceptor such as oxygen is present, *Escherichia coli* undergoes breathing and not fermentation. Only in the absence of an electron acceptor such as oxygen, *Escherichia coli* gains energy (ATP) only by phosphorylation at substrate level, and produces reductive organic acids such as lactic acid using reduction power (NADH) obtained in the glycolytic pathway. For reasons such as these, conventional D-lactic acid fermentation using *Escherichia coli* is carried out mostly in anaerobic culture. In the rare case, bi-phasic culture is carried out wherein the first half of the culture is aerated and the second half of the culture is anaerobic. However, this means that the first half is performed for the purpose of ensuring a sufficient amount of microbial mass, and the final lactic acid fermentation is carried out under anaerobic conditions as expected. However, when actual industrial production is supposed, corn steep liquor (hereinafter, may be simply referred to as CSL) or the like, which is a cheap amino acid source added to a medium, contain not only organic acids which become impurities, but also both of D-isomer and L-isomer of lactic acid. However, if anaerobic culture is carried out, L-lactic acid is not assimilated and remains in the medium. L-lactic acid dehydrogenase (hereinafter, may be simply referred to as lld), which is a catalytic enzyme of the reaction to produce pyruvic acid from L-isomer, is known to be expressed under aerobic conditions. Therefore, if there is a method to ferment lactic acid in good efficiency even under aerobic conditions, it is expected that the method would enable to assimilate L-isomer contained in the medium into microbial mass, and to produce D-isomer with high optical purity. However, there has been no technique so far to realize it.

Before of the report by Zhou, et al. about lactic acid production using a pfl disrupted strain, there have been the following reports. Specifically, Contag, et al. (Contag, P. R., et. al., Appl. Environ. Microbiol., Vol. 56(12), pp 3760-3765 (1990)) have shown that, while pfl non-variant *Escherichia coli* strain produces 35 mM of lactic acid, a pfl variant strain produces 45 mM of lactic acid due to improved productivity of lactic acid. Namely, it has been already known by disclosure of data by Contag, et al. that D-lactic acid productivity is improved by inactivation of pfl activity in *Escherichia coli*.

D-lactate dehydrogenase is classified into NADH-dependent one and FAD-dependent one according to the difference in the dependence on a coenzyme. NADH-dependent D-lactate dehydrogenase catalyzes a reaction from pyruvic acid to D-lactic acid in the living body. Especially, *Escherichia coli*-derived NADH-dependent D-lactate dehydrogenase is called ldhA.

Yang, et al. (Yang, Y. T., et. al., Metab. Eng., Vol. 1(2), pp 141-152 (1999)) have reported that, by introducing an expression vector incorporated with ldhA gene into *Escherichia coli*, the amount of D-lactic acid accumulated is improved, albeit small, to about 8 g/L. That is, it is known from data disclosed by Yang, et al. that D-lactic acid productivity is improved by reinforcement of ldhA activity in *Escherichia coli*.

On the other hand, according to Bunch, et al. [Bunch, P K., Microbiology, Vol. 143(Pt 1), 187-195 (1997)], it has been reported that *Escherichia coli*, into which an expression vector of *Escherichia coli*-derived ldhA gene is introduced, is inhibited in growth thereof by the introduced expression vector.

In addition, examples of over-expression in *Escherichia coli* of D-lactate dehydrogenase (hereinafter, may be called ldh) derived from bacteria other than *Escherichia coli*, include expression of *Lactobacillus helveticus*-derived ldh reported by Kochhar, et al. [Kochhar, S., Eur. J. Biochem., (1992) 208, 799-805], and expression of *Lactobacillus bulgaricus*-derived ldh reported by Kochhar, et al. [Kochhar, S., Biochem. Biophys. Res. Commun., (1992) 185, 705-712]. However, in any of the reports, there is no mention about the amount of D-isomer or of pyruvic acid accumulated, since these reports were concerned with investigation on physico-chemical properties of the expressed enzymes.

However, D-lactic acid productivity of a microorganism which is inactivated or decreased in pfl activity, and further reinforced in ldhA activity have not been still well known.

With a method for reinforcing a gene using an expression vector, troubles may happen generally such as loss of the vector causing decrease in the amount of a desired gene expressed, and further decrease in the productivity of a desired substance. From these findings, the method for reinforcing an ldh gene using an expression vector has several problems to be solved in application to industrial production of D-lactic acid, and a method for reinforcing a gene is desired to replace it. However, no report has been made about such approach.

As a method for reinforcing a gene instead of using an expression vector, there is a method for reinforcing the gene wherein the gene promoter region on the genome is substituted by an arbitrary promoter as reported by Solem, et al. (Solem, C., et. al., Appl. Environ. Microbiol., Vol. 68(5), pp 2397-2403 (2002)). However, if a case is considered in which this technique is applied to production of D-lactic acid in which the above-mentioned ldhA gene is used, the ldhA gene reinforced with this method is only 1 copy of the gene on the genome. Thus, it is predicted that ldha activity improvement is small as compared with a reinforcement method by an expression vector which expresses many copies of the gene, so it has been difficult even for a person skilled in the art to anticipate that the D-lactic acid productivity improves as compared with the case of using the expression vector.

On the other hand, it has been disclosed by an analysis of enzyme purified from *Escherichia coli* that FAD-dependent D-lactate dehydrogenase (hereinafter, may be simply referred to as dld) catalyzes mainly the reverse reaction of NADH-dependent D-lactate dehydrogenase, i.e., the reaction from D-lactic acid to pyruvic acid. Shaw, et al. acquired in the past *Escherichia coli* strains JS150 and JS151, wherein dld was disrupted. However, there was no mention about D-lactic acid productivity or pyruvic acid productivity in those strains (Shaw, L., et. al., J. Bacteriol., Vol. 121(3), pp 1047-1055 (1975)). In addition, Barnes, et al. have reported that dld is involved in incorporation of a variety of amino acids or saccharides (Barnes, E. M., et. al., J. Biol. Chem., Vol. 246(17), pp 5518-5522 (1971)]. However, there was no mention about D-lactic acid or pyruvic acid production.

In addition, if a search is conducted for the double variant of dld and pfl with the database of Yale university-affiliated *E. coli* Genetic Stock Center (CGSC), which is one of authorities for delivery of an *Escherichia coli* strain, it gives an article by Mat-Jan, et al., (Mat-Jan, F., et. al., J. Bacteriol., Vol. 171(1), pp 342-348 (1989)] as the corresponding item. However, as the results of actual close examination, there was no description about disrupted double strain of dld and pfl in this article.

As described above, there has been no report for D-lactic acid to indicate achievement of productivity and selectivity at the same time corresponding to industrial level by fermentation production using a microorganism, and also there were no previous examples in which, for example, succinic acid or fumaric acid, which is a main by-product organic acid, was reduced while maintaining high D-lactic acid productivity.

Thus, we have intensively studied in order to suppress succinic acid production without decreasing D-lactic acid productivity, and as a result have found that, by disruption of gene of malate dehydrogenase (hereinafter, may be called mdh), which is an enzyme catalyzing a reaction from oxalacetic acid to malic acid under anaerobic conditions, it is possible to suppress completely production of succinic acid without decreasing D-lactic acid productivity. However, since fumaric acid was still produced as a by-product, we have also found that it is possible to decrease the amount of by-product of fumaric acid by disruption of the gene of aspartate ammonia-lyase (hereinafter, may be called aspA).

An inactivation effect of mdh activity has been disclosed in the article of Courtright, et al. in 1970 (Courtright, J. B. et. al., J. Bacteriol., Vol. 102(3), pp 722-728 (1970)). The disclosed findings indicate that, with *Escherichia coli* wherein mdh activity is inactivated, while there is no reactivity from oxalacetic acid to malic acid under anaerobic conditions, reactivity from aspartic acid to fumaric acid is improved in contrast. That is, this explains that there are two pathways to produce succinic acid under anaerobic conditions, i.e., a pathway to lead to fumaric acid and succinic acid via malic acid from oxalacetic acid, and a pathway to lead to fumaric acid and succinic acid via aspartic acid from oxalacetic acid, and that if mdh activity is inactivated, the former pathway comes to a stop, but the latter pathway is activated in contrast. Therefore, the article of Courtright, et al. is not a disclosure showing that succinic acid is not produced by inactivation of the mdh activity.

Another prior art on the effects of inactivation of mdh activity relates to yeast in which the mdh gene is disrupted (JP-A No. 11-056361). This patent relates to change of the amount of malic acid produced by disruption of the mdh gene of the yeast, but has no mention on how such results affect the amount of succinic acid produced.

In summary, it has been difficult even for a person skilled in the art to assume from the findings in the past that succinic acid production can be completely suppressed by inactivation of mdh of a microorganism.

In addition, concerning the effect of inactivation of aspA activity, only findings on *Yersinia pestis* have been disclosed in the past (Dreyfus, L. A., et. al., J. Bacteriol., Vol. 136(2), pp 757-764 (1978)). However, the gist of the present article is that aspartic acid or glutamine becomes less susceptible to decomposition in the cell by inactivation of aspA activity, and there is no discussion about the amount of fumaric acid produced.

Patent Document 1: JP-A No. 11-056361
Non-Patent Document 1: Chang, D.-E., et. al., Appl. Environ. Microbiol., Vol. 65(4), pp 1384-1389 (1999)
Non-Patent Document 2: Zhou, S., et. al., Appl. Environ. Microbiol., Vol. 69(1), pp 399-407 (2003)
Non-Patent Document 3: Contag, P. R., et. al., Appl. Environ. Microbiol., Vol. 56(12), pp 3760-3765 (1990)
Non-Patent Document 4: Yang, Y. T., et. al., Metab. Eng., Vol. 1(2), pp 141-152 (1999)
Non-Patent Document 5: Bunch, P. K., et. al., Microbiology, Vol. 143(Pt 1), pp 187-195 (1997)
Non-Patent Document 6: Kochhar, S., et. al., Eur. J. Biochem., Vol. 208(3), pp 799-805 (1992)
Non-Patent Document 7: Kochhar, S., et. al., Biochem. Biophys. Res. Commun., Vol. 185(2), pp 705-712 (1992)
Non-Patent Document 8: Solem, C., et. al., Appl. Environ. Microbiol., Vol. 68(5), pp 2397-2403 (2002)
Non-Patent Document 9: Shaw, L., et. al., J. Bacteriol., Vol. 121(3), pp 1047-1055 (1975)
Non-Patent Document 10: Barnes, E. M., et. al., J. Biol. Chem., Vol. 246(17), pp 5518-5522 (1971)
Non-Patent Document 11: Mat-Jan, F., et. al., J. Bacteriol., Vol. 171(1), pp 342-348 (1989)
Non-Patent Document 12: Courtright, J. B. et. al., J. Bacteriol., Vol. 102(3), pp 722-728 (1970)
Non-Patent Document 13: Dreyfus, L. A., et. al., J. Bacterial., Vol. 136(2), pp 757-764 (1978)

DISCLOSURE OF THE INVENTION

One subject of the present invention is to provide a method for high-producing D-lactic acid, and another subject of the invention is to provide a method for producing D-lactic acid with high selectivity, in which optical purity is high and a by-product organic acid is small.

Another subject of the invention is to provide a method for producing D-lactic acid with a reduced amount of pyruvic acid accumulated, wherein pyruvic acid is an impurity organic acid and has not been simply removed conventionally from the medium in which lactic acid is produced and accumulated by a microorganism.

Another subject of the invention is to provide a method for producing lactic acid, comprising producing lactic acid efficiently by using hetero-lactic acid fermentation bacteria. Another subject of the invention is to provide a method for producing lactic acid, comprising producing lactic acid efficiently with high optical purity using hetero-lactic acid fermentation bacteria.

Another subject of the invention is to provide a method for producing D-lactic acid, wherein production of succinic acid and/or fumaric acid, which is a by-product, is suppressed without decrease in productivity of the desired substance.

Another subject of the invention is to provide a method of reinforcing stable D-lactate dehydrogenase gene instead of a method of reinforcing using an expression vector, and a method for producing D-lactic acid in higher yield.

The present inventors have studied intensively to solve the above-mentioned subjects, and as a result, have found that a bacteria, in which activity of pyruvate formate-lyase (pfl) is inactivated or decreased, and activity of *Escherichia coli*-derived NADH-dependent D-lactate dehydrogenase (ldhA) is enhanced, produces D-lactic acid in a shorter time than conventional one, and achieves a high amount of accumulation that has not been possible so far. Especially, with regard to a method for enhancing ldhA activity, it has found that it is possible to produce a remarkable amount of D-lactic acid in a shorter time by using a microorganism which expresses a gene encoding ldhA on the genome by linking with a promoter of a gene which controls expression of a protein involved in a glycolytic pathway, a nucleic acid biosynthesis pathway or an amino acid biosynthesis pathway, as compared with the method for enhancing the gene expression using the expression vector. In the method using the expression vector, the expression level of D-lactate dehydrogenase in a cell is higher than that in the method of the present invention, but this high amount of the enzyme is not directly related to high production of D-lactic acid for some reason. In contrast, it is very surprising that the D-lactic acid productivity in the present invention is dramatically improved eventually although the expression level of the enzyme in a cell is not so high.

Next, the inventors have found that a part of pyruvic acid present in a microorganism culture solution is actually produced by did from D-lactic acid, and further have found that, by breeding and culturing a microorganism wherein the dld gene is substantially inactivated or decreased, growth of the microorganism is not suppressed as compared with the host, and that a culture solution containing high quality D-lactic acid is obtained, wherein the concentration of pyruvic acid contained in the medium is decreased. Furthermore, they have found that, by breeding and culturing a microorganism wherein the pfl activity is inactivated or decreased, and/or the ldhA activity is enhanced, and further the did gene is substantially inactivated or decreased, high quality D-lactic acid is obtained with decreased pyruvic acid in the medium.

Furthermore, the inventors have accomplished the present invention by finding that the above-mentioned microorganism having a TCA cycle, wherein activity of malate dehydrogenase (mdh) is inactivated or decreased, and further aspartate ammonia-lyase (aspA) activity is inactivated or decreased, suppresses by-production of succinic acid and fumaric acid while maintaining high D-lactic acid productivity.

Specifically, the present invention is as follows.

[1] A method for producing lactic acid, which comprises culturing a hetero-lactic acid fermentation bacteria, wherein activity of pyruvate formate-lyase (pfl) is inactivated or decreased, on a medium to which two or more kinds of amino acids are added, and recovering lactic acid from the obtained culture.

[2] The method for producing lactic acid as described in [1], wherein the hetero-lactic acid fermentation bacteria is *Escherichia coli*.

[3] The method for producing lactic acid as described in [2], wherein *Escherichia coli* is MT-10934 (FERM BP-10057) strain.

[4] A method for producing D-lactic acid, which comprises culturing a bacteria, wherein activity of *Escherichia coli*-derived NADH-dependent D-lactate dehydrogenase (ldhA) is enhanced and activity of pyruvate formate-lyase (pfl) is inactivated or decreased, and recovering D-lactic acid from the obtained culture.

[5] The method for producing D-lactic acid as described in [4], wherein the bacteria is *Escherichia coli*.

[6] The method for producing D-lactic acid as described in [4] or [5], wherein culture is carried out on a medium to which two or more kinds of amino acids are added.

[7] A microorganism in which activity of FAD-dependent D-lactate dehydrogenase (dld) inherent in the microorganism is inactivated or decreased, activity of pyruvate formate-lyase (pfl) is inactivated or decreased, and/or activity of *Escherichia coli*-derived NADH-dependent D-lactate dehydrogenase (ldhA) is enhanced.

[8] The microorganism as described in [7], wherein the microorganism is a bacteria.

[9] The microorganism as described in [8], wherein the bacteria is *Escherichia coli*.

[10] A method for producing D-lactic acid, which comprises culturing the microorganism as described in any one of [7] to [9] in a liquid medium, wherein D-lactic acid is produced, accumulated, and isolated from the liquid medium.

[11] The method for producing D-lactic acid as described in [10], wherein culture is carried out on a medium to which two or more kinds of amino acids are added.

[12] A method for producing D-lactic acid, which comprises culturing a microorganism in which activity of FAD-dependent D-lactate dehydrogenase (dld) is inactivated or decreased, in a liquid medium, wherein D-lactic acid is produced, accumulated, and isolated from the liquid medium.

[13] The method as described in [12], wherein the microorganism is a bacteria.

[14] The method as described in [13], wherein the bacteria is *Escherichia coli*.

[15] A microorganism, wherein a gene encoding *Escherichia coli*-derived NADH-dependent D-lactate dehydrogenase (ldhA) expresses the NADH-dependent D-lactate dehydrogenase (ldhA) on the genome of the microorganism by using a promoter of a gene which controls expression of a protein involved in a glycolytic pathway, a nucleic acid biosynthesis pathway or an amino acid biosynthesis pathway.

[16] The microorganism as described in [15], wherein the microorganism is *Escherichia coli*.

[17] The microorganism as described in [15] or [16], wherein activity of pyruvate formate-lyase (pfl) inherent in the microorganism is inactivated or decreased, and/or activity of FAD-dependent D-lactate dehydrogenase (dld) is inactivated or decreased.

[18] *Escherichia coli*, which expresses *Escherichia coli*-derived NADH-dependent D-lactate dehydrogenase (ldhA) on the genome of *Escherichia coli* by using a promoter of an *Escherichia coli*-derived gene which controls expression of a protein involved in a glycolytic pathway, a nucleic acid biosynthesis pathway or an amino acid biosynthesis pathway, instead of using a promoter of a gene encoding the NADH-dependent D-lactate dehydrogenase (ldhA).

[19] *Escherichia coli* as described in [18], wherein the promoter of the *Escherichia coli* gene, which controls expression of the protein involved in the glycolysis pathway, the nucleic acid biosynthesis pathway or the amino acid biosynthesis pathway, is a promoter of an *Escherichia coli*-derived glyceraldehyde-3-phophate dehydrogenase gene.

[20] *Escherichia coli* as described in [18] or [19], wherein activity of pyruvate formate-lyase (pfl) inherent in the *Escherichia coli* is inactivated or decreased, and/or activity of FAD-dependent D-lactate dehydrogenase (dld) is inactivated or decreased.

[21] A method for producing D-lactic acid, which comprises culturing the microorganism as described in any one of [15] to [20] using a medium.

[22] A microorganism having a TCA cycle, wherein activity of malate dehydrogenase (mdh) is inactivated or decreased, activity of pyruvate formate-lyase (pfl) is inactivated or decreased, and/or activity of FAD-dependent D-lactate dehydrogenase (dld) is inactivated or decreased.

[23] The microorganism as described in [22], wherein activity of aspartate ammonia-lyase (aspA) inherent in the microorganism is inactivated or decreased.

[24] The microorganism as described in [22] or [23], wherein the microorganism is a bacteria.

[25] The microorganism as described in [24], wherein the bacteria is *Escherichia coli*.

[26] The microorganism as described in [25], wherein activity of *Escherichia coli*-derived NADH-dependent D-lactate dehydrogenase (ldhA) is enhanced.

[27] A method for producing a compound other than an organic acid formed in a TCA cycle, which comprises culturing the microorganism as described in any one of [22] to [26] by using a medium.

[28] The method as described in [27], wherein the compound other than the organic acid is D-lactic acid.

[29] The method for producing lactic acid as described in any one of [1] to [6], [10] to [14], [21] and [28], wherein culture is carried out under aerobic conditions.

[30] The method for producing lactic acid as described in [29], wherein the aerobic conditions enable supply of oxygen which satisfies a requirement of an oxygen-transfer coefficient not less than $K_L a$ of $1\ h^{-1}$ and not more than $400\ h^{-1}$ at normal pressure using water at a temperature of 30° C.

[31] The method for producing lactic acid as described in any one of [1] to [6], [10] to [14], [21] and [28] to [30], wherein the culture pH is 6 to 8.

According to the present invention, a microorganism having high D-lactic acid productivity and D-lactic acid selectivity is provided. Thus, by culturing the microorganism prepared by the invention to produce D-lactic acid, it is possible to produce D-lactic acid with high purity more economically, as compared with the conventional method.

Further, according to the present invention, a bacteria producing D-lactic acid is provided, wherein the amount of pyruvic acid produced is small. Thus, by culturing the strain prepared by the invention to produce D-lactic acid, it is possible to produce D-lactic acid with high chemical purity and high optical purity more economically, as compared with the conventional method.

Further, by producing D-lactic acid by using the microbial mass prepared according to the present invention, it becomes possible to produce D-lactic acid fermentation solution with high quality and less purification load, wherein the content of pyruvic acid, which is an impurity, is decreased compared to the conventional method.

Further, according to the present invention, it becomes possible to suppress by-production of succinic acid and/or fumaric acid without causing decrease in productivity of a compound other than organic acids produced in a TCA cycle. Especially, in the case where the purpose is to produce industrially a compound other than the organic acids produced in the TCA cycle, it is possible to reduce the purification cost of the desired substance by decreasing the kind and amount of by-products.

BEST MODE FOR CARRYING OUT THE INVENTION

Figure 1:
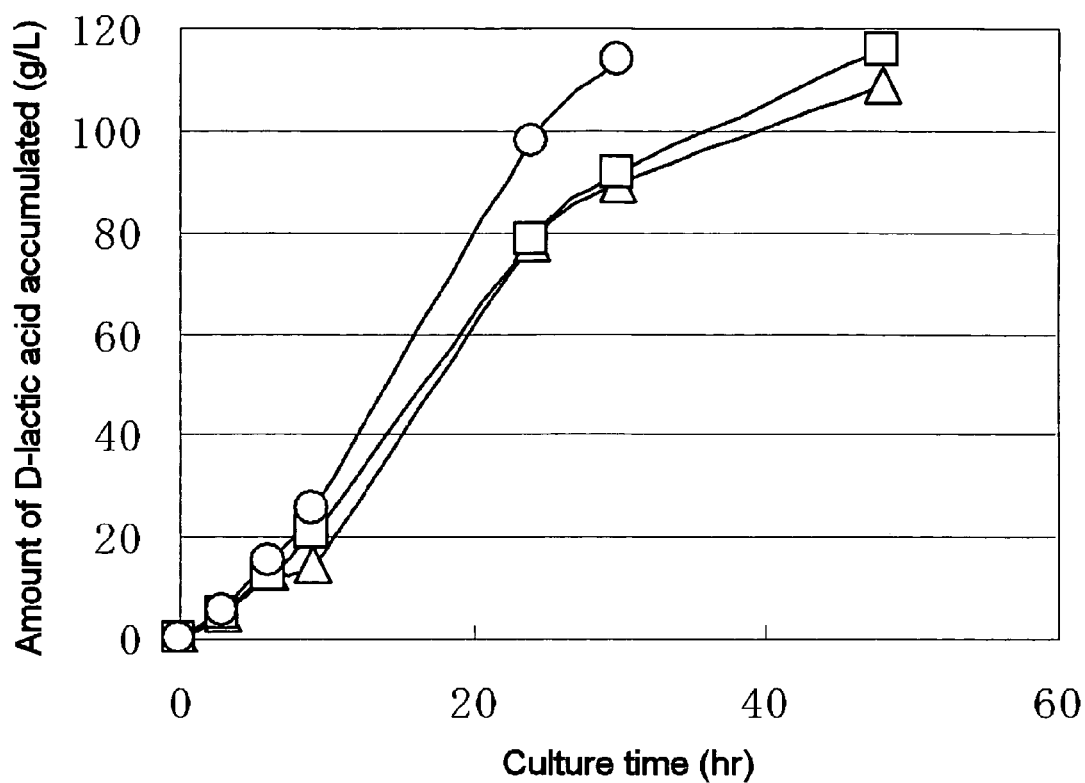
FIG. 1 is a graph which shows the time course of an amount of D-lactic acid accumulated in the culture solution in Example 20. In the figure, the triangle shows the results of MG1655ΔpflΔdld strain (Example 15), the square shows the results of MG1655ΔpflΔdld/pGAPldhA strain (Example 18) and the circle shows the results of MG1655ΔpflΔdld/GAPpldh genome-inserted strain (Example 19).

Hereinafter, the present invention will be explained in detail.

Pyruvate formate-lyase (pfl) in the present invention is an enzyme classified into the enzyme number 2.3.1.54 based on the report of the enzyme committee of International Union of Biochemistry (I.U.B.), which is also called formate acetyl transferase. The present enzyme refers to a generic name of an enzyme which reversibly catalyzes a reaction to produce formic acid from pyruvic acid.

Inactivation in the present invention refers to a state in which activity of the above-mentioned enzyme measured by the conventional measurement system is below the detection limit.

Decrease in the present invention refers to a state in which activity of the above-mentioned enzyme is decreased significantly due to mutation of a gene encoding the above-mentioned enzyme and/or genetic recombination, than the state before conducting those treatments.

The hetero-fermentation bacteria in the present invention refers to a bacteria capable of producing at least one or more kinds of substances selected from formic acid, acetic acid, succinic acid and ethanol in addition to lactic acid by decomposing saccharide in fermentation. Specifically, as the hetero-fermentation bacteria of the present invention, *Escherichia coli* is suitable. As the hetero-fermentation bacteria wherein activity of pyruvate formate-lyase (pfl) is inactivated or decreased, a pfl gene-disrupted strain of any *Escherichia coli* wild strain or *Escherichia coli* MT-10934, which can be prepared in the method shown according to Examples of the present invention or the like, can be exemplified.

The above-mentioned MT-10934 is a strain in which pfl activity is confirmed to be already decreased, so it is possible to perform the present invention easily. The present strain has been deposited on Nov. 8, 2002 as the deposition number FERM BP-10057 at International Patent Organism Depositary, Tsukuba Central 6, 1-1-1 Higashi, Tsukuba, Ibaraki, of National Institute of Advanced Industrial Science and Technology, based on the Budapest Treaty on the International Recognition of the Deposit of Microorganisms for the Purposes of patent Procedure.

In addition, concerning the pfl single variant strain, since MT-10934 has properties of HfrC, it is mixed with a wild strain having arbitrary F— properties, for example, MG1655, W3110 or the like in an LB medium for 2 hours, and then diluted to acquire single colonies, from which a pfl single variant strain may be selected for a desired variant strain. Since the amount of formic acid produced is decreased in the anaerobic culture as compared to the wild strain, the pfl variant strain can be also acquired by selection using this as an index.

The culturing in the present invention refers to culturing a microorganism related to the present invention using a medium. In this case, the medium to be used is not particularly limited if it is a medium containing traces of organic components, nucleic acids, vitamins or the like, which are required by the microorganism to produce carbon source, nitrogen source, inorganic ion and lactic acid.

The medium to which two or more kinds of amino acids are added in the present invention means a medium which contains at least two or more kinds among various amino acids in the nature, and includes a medium which contains a natural product such as yeast extracts, casamino acid, peptone, whey, blackstrap molasses, corn steep liquor and the like or hydrolysates of natural product extracts. To obtain more preferable results, the medium comprises preferably from 0.5% to 20%, and further preferably from 2% to 15% of at least one kind selected from yeast extracts, peptone, whey, blackstrap molasses and corn steep liquor, or a mixture thereof. Especially, addition of corn steep liquor gives a great effect, and in this case, better results may be obtained without adding a salt such as ammonium sulfate than otherwise. The medium is usually a liquid medium.

The culture condition is varied depending on prepared microbial mass and a culture apparatus. For example, when MT-10934 with decreased pfl activity is decreased, the culture is performed under the following conditions in which the culture temperature is preferably from 20° C. to 40° C., more preferably from 25° C. to 35° C., and pH is adjusted to preferably 6.0 to 7.2, more preferably 6.5 to 6.9 with NaOH, $NH_3$ or the like. The culture time is not particularly limited, but it is a time necessary to grow the microbial mass sufficiently, and further produce lactic acid.

In addition, in the case of using the pfl gene-disrupted strain of the Escherichia coli wild strain MG1655 wherein pfl activity is inactivated, neutral or from neutral to somewhat alkaline pH gives maximum productivity, and the culture pH is preferably from 6.9 to 7.4, and more preferably from 7.1 to 7.3. The culture temperature is allowed to be higher than that of MT-10934, and therefore culture at 33° C. to 42° C. can give a maximum productivity.

In the culture, a fermentor is generally used in culturing, which can usually control temperature, pH, aerobic conditions and stirring speed, but the culture of the present invention is not limited to the use of the fermentor. In the case of culture using the fermentor, if necessary, seed culture is carried out in advance as preculture, and this may be inoculated in a needed amount on a medium in a fermentor prepared in advance.

MT-10934 may produce formic acid in a pH region of pH 7 to 7.5, while for the pfl gene-disrupted strain of MG1655, production of formic acid is not found in the culture method of the present invention. Therefore, in the case of using Escherichia coli as hetero-fermentation bacteria, a maximum productivity can be obtained under the following conditions; when production of formic acid is observed as in MT-10934 in case of producing lactic acid with the adopted microbial mass using a medium of about neutral pH, pH of the medium is controlled from neutral to somewhat acidic side in actual lactic acid production, and, when production of formic acid is not observed as in the pfl gene-disrupted strain of MG1655, pH of the medium is controlled to neutral or somewhat alkaline side in actual production of lactic acid.

The culture in the present invention refers to microbial mass, a culture solution, and a treatment product thereof, which are produced by the method described above.

A method of recovering lactic acid from the culture such as the culture solution obtained above, for example, includes conventionally known method if it is from the culture solution, for example, a method of direct distillation after acidification, a method of lactide formation and distillation, a method of distillation after adding alcohol and catalyst for esterification, a method of extraction in an organic solvent, a method of isolation with an ion exchange column, a method of concentration and isolation by electrodialysis or the like or a combination thereof. In addition, since the microbial mass produced by the method of the present invention produces an enzyme group which is suitable for lactic acid production, producing lactic acid further by using the enzyme group and recovering the produced lactic acid is also regarded as a part of the method of recovering lactic acid from the culture.

Escherichia coli-derived NADH-dependent D-lactate dehydrogenase (ldhA) in the present invention is an Escherichia coli-derived enzyme which produces D-lactic acid and NAD from pyruvic acid and NADH, and specifically exemplified by an enzyme produced from a gene acquired by Bunch, et al. (Microbiology 143 (Pt 1), 187-195 (1997)), or a gene having the sequence contained in the DNA fragments amplified by PCR from SEQ ID NO: 3 and SEQ ID NO: 4 with the genome DNA of Escherichia coli as a template.

Enhancement of ldhA activity in the present invention refers to a state in which activity of the enzyme produced from the gene encoding ldhA is increased more significantly by mutation of the gene encoding ldhA and/or genetic recombination, than the state before conducting those treatments.

The bacteria in the present invention is generally a microorganism of a prokaryotic cell.

As an example of the bacteria in the present invention wherein ldha activity is enhanced and further pfl activity is inactivated or decreased, MT-10934/pGlyldhA can be exemplified, which is described in Examples of the invention. The present strain can be used suitably in the method for producing lactic acid as described in the above-mentioned [1], which comprises culturing a hetero-lactic acid fermentation bacteria, wherein the activity of pyruvate formate-lyase (pfl) is inactivated or decreased, in a medium to which two or more kinds of amino acids are added, and recovering lactic acid from the obtained culture.

As one of the measures to enhance ldhA activity in the present invention, effective is a method in which a gene encoding ldhA is integrated into an expression plasmid as linked to a promoter of a gene which controls expression of a protein involved in a glycolytic pathway, a nucleic acid biosynthesis pathway or an amino acid biosynthesis pathway, and introduced into a desired bacteria. In this case, the promoter of the gene which controls expression of the protein involved in the glycolytic pathway, the nucleic acid biosynthesis pathway or the amino acid biosynthesis pathway refers to a strong promoter which functions constantly in a bacteria, preferably in Escherichia coli, and is less susceptible to suppression of expression even in the presence of glucose. Specific examples thereof include a promoter of glyceraldehyde-3-phosphate dehydrogenase or a promoter of serine hydroxymethyltransferase (glyA). The bacteria obtained in this manner makes it possible to improve the amount of D-lactic acid accumulated, reduce the concentration of pyruvic acid which is an impurity, and improve optical purity of D-lactic acid in the production of D-lactic acid under aerobic conditions, compared to those in which ldhA expression is not enhanced.

The FAD-dependent D-lactate dehydrogenase (dld) in the present invention refers to a generic name of an enzyme that catalyzes a reaction to produce pyruvic acid from D-lactic acid in the presence of oxidized flavin adenine dinucleotide, which is a coenzyme.

The microorganism in the present invention is not particularly limited if the microorganism is capable of producing D-lactic acid, and also includes a microorganism which becomes capable of producing D-lactic acid by any modification although the microorganism is initially incapable of producing D-lactic acid.

The microorganism wherein did activity is inactivated or decreased according to the present invention, and/or pfl activity is inactivated or decreased, and/or ldhA activity is enhanced, can be exemplified by an *Escherichia coli* MT-10994 (FERM BP-10058) strain.

The promoter of the gene which controls expression of the protein involved in the glycolytic pathway, the nucleic acid biosynthesis pathway or the amino acid biosynthesis pathway in the present invention, is a strong promoter which constantly functions in a microorganism, and is less susceptible to suppression of expression even in the presence of glucose. Specific examples include a promoter of glyceraldehyde-3-phophate dehydrogenase (hereinafter, may be called GAPDH) or a promoter of serine hydroxymethyltransferase.

The promoter in the present invention refers to a site, to which RNA polymerase having a sigma factor is bound and initiates transcription. For example, an *Escherichia coli*-derived GAPDH promoter is described in Base Nos. 397 to 440 in the base sequence information of GenBank accession number X02662.

The microorganism according to the present invention wherein the gene encoding ldha expresses the ldhA on the genome by using the promoter of the gene which controls expression of the protein involved in the glycolytic pathway, the nucleic acid biosynthesis pathway or the amino acid biosynthesis pathway, and wherein pfl activity is inactivated or decreased, and/or did activity is inactivated or decreased, can be exemplified by an *Escherichia coli* MT-10994 (FERM BP-10058) strain.

Since the *Escherichia coli* MT-10994 strain is expressed by functionally linking the ldhA gene to the GAPDH promoter on the genome, and pflB and dld are inactivated by gene disruption, the present invention can be carried out easily using this strain. The present strain has been deposited on Mar. 19, 2004 as the deposition number FERM BP-10058 at International Patent Organism Depositary, Tsukuba Central 6, 1-1-1 Higashi, Tsukuba, Ibaraki, of National Institute of Advanced Industrial Science and Technology, based on the Budapest Treaty on the International Recognition of the Deposit of Microorganisms for the Purposes of patent Procedure.

The TCA cycle in the present invention means a metabolic pathway for eventually undergoing complete oxidation of carbon skeletons such as glucose, fatty acid and many amino acids, which is also called a citric acid cycle, a tricarboxylic acid cycle or a Krebs cycle.

The malate dehydrogenase (mdh) in the present invention is classified into the enzyme number 1.1.1.37, based on the report of the enzyme committee of International Union of Biochemistry (I.U.B.), and refers to a generic name of an enzyme, which reversibly catalyzes a reaction to produce oxalacetic acid from malic acid in the presence of oxidized nicotinamide adenine dinucleotide which is a coenzyme.

The microorganism wherein mdh activity is inactivated or decreased in the present invention, wherein pfl activity is inactivated or decreased, and/or dld activity is inactivated or decreased, can be exemplified by the *Escherichia coli* MT-10994 strain. The present strain can be used suitably in the method for producing lactic acid as described in the above-mentioned [1], which comprises culturing a heterolactic acid fermentation bacteria, wherein activity of pyruvate formate-lyase (pfl) is inactivated or decreased, in a medium to which two or more kinds of amino acids are added and recovering lactic acid from the obtained culture.

The aspartate ammonia-lyase (aspA) in the present invention is classified into the enzyme number 4.3.1.1 based on the report of the enzyme committee of International Union of Biochemistry (I.U.B.), which is also called aspartame. The present enzyme refers to a generic name of an enzyme which reversibly catalyzes a reaction to produce fumaric acid from L-aspartic acid.

When lactic acid is produced by culturing the microorganism obtained in the present invention, aeration may be carried out to obtain more preferable results though aeration may not be necessary at all. The aeration conditions herein do not always require the air to pass through the culture solution, but also include surface aeration depending on the shape of the fermentor, wherein an air layer above the culture solution is ventilated while the culture solution is stirred moderately, and refer to flowing a gas containing oxygen into the fermentor. In the case of aeration into the solution, since dissolved oxygen concentration changes according to combinations of internal pressure, stirring blade location, stirring blade shape and stirring speed, optimal conditions can be found as follows by using lactic acid productivity, amount of organic acids other than lactic acid or the like as an index. For example, in the case of culturing *Escherichia coli* MT-10934 strain with a relatively small fermentor such as BMJ-01, a culture apparatus manufactured by ABLE Corporation, preferable results can be obtained under aeration conditions which can be achieved with the aeration rate of 0.01 vvm to 1 vvm and the stirring speed of 50 rpm to 500 rpm at normal pressure, more preferably, the aeration rate of 0.1 vvm to 0.5 vvm and the stirring speed of 100 rpm to 400 rpm at normal pressure when 500 g of the culture solution is used. This aerobic condition is a condition which enables supply of oxygen satisfying a requirement of an oxygen-transfer coefficient $K_L a$ of not less than 1 $h^{-1}$ or not more than 400 $h^{-1}$ at normal pressure using water at a temperature of 30° C.

Further, another index of optimal aeration condition is an aeration condition achieved by the aeration rate and the stirring speed under which formic acid, acetic acid, succinic acid and ethanol, which are produced by the MT-10934 strain in anaerobic culture, is not more than 5.0 g/L, and more preferably not more than 1.0 g/L, and further lactic acid is produced.

Further, another index of optimal aeration condition is a condition achieved by the aeration rate and the stirring speed under which the concentration of L-lactic acid decreases to not more than 0.02% within 10 to 100 hours when the MT-10934 strain is cultured in a medium containing 0.3% L-lactic acid, which is an optical isomer.

The aeration condition as described above does not need to be carried out throughout from the start to the end of the culture, and carrying out in a part of the culture process can also give preferable results.

In addition, by conducing aeration as described above, lactic acid productivity can be improved and reduction of the optical isomer can be achieved.

Hereinafter, an example of the present invention is shown by Examples, which does not limit the present invention by any means.

EXAMPLE 1

Production of Lactic Acid by MT-10934 Strain

The composition of the medium used in culture is described in Table 1 as below.

TABLE 1

| Medium composition | |
|---|---|
| Glucose | 10% |
| Corn Steep Liquor (manufactured by NIHON SHOKUHIN KAKO CO. LTD.) | 5% |
| Ammonium sulfate | 0.5% |
| Disodium hydrogen phosphate 12-hydrate | 0.3% |
| Potassium dihydrogen phosphate | 0.15% |
| Sodium chloride | 0.15% |
| Magnesium sulfate 7-hydrate | 0.1% |
| Adecanol LG126 | 0.1% |

The present medium contains 0.34% of reducing sugar estimated as hydrolyzed product, 0.31% of D-lactic acid, 0.31% of L-lactic acid, 0.33% of free amino acids and trace amount of various organic acids, all of which derived from corn steep liquor.

Escherichia coli MT-10934 strain was inoculated into 25 ml of an LB Broth, Miller's culture solution (Difco244620) contained in a conical flask, and culture was carried out with stirring overnight with 120 rpm as preculture. Then, the whole amount was inoculated into 475 g of the medium of the above-mentioned composition contained in a 1 L-fermentor (BMJ-01, culture apparatus manufactured by ABLE Corporation). Culture was carried out under the conditions including atmospheric pressure, an aeration rate of 0.5 vvm, a stirring speed of 150 rpm, a culture temperature of 31° C. and pH of 6.7 (adjusted with NaOH), until glucose was completely consumed.

After completing the culture, assay of the organic acids and measurement of optical purity of D-lactic acid in the obtained culture solution were performed with HPLC according to an established method. The results are shown in Table 2.

TABLE 2

|  | MG1655 (wild) | MT-10934 |
|---|---|---|
| Amount of D-lactic acid accumulated | 54.9 g/kg of culture solution | 90.5 g/kg of culture |
| Recovered amount of culture solution | 540 g | 570 g |
| Weight of dry microbial mass | 3.5 g/L | 2.2 g/L |
| Optical purity of D-lactic acid | 99.9% ee or more | 99.9% ee or more |
| Succinic acid | 6.2 g/L | N.D <0.2 g/L |
| Formic acid | 1.8 g/L | N.D <0.1 g/L |
| Acetic acid | 2.4 g/L | N.D <0.1 g/L |
| Ethanol | 0.8 g/L | N.D <0.1 g/L |
| Amount of D-lactic acid accumulated after 50 hrs of culture initiation | 46.5 g/kg | 58.2 g/kg |

N.D: Not detected

In the results, the reason why the total amount of lactic acid is more than the amount of glucose added at culture initiation is considered to be that the carbon source in corn steep liquor was used. However, using all the reducing sugar, organic acids and amino acids in corn steep liquor, the conversion rate of 90% or more was reached. In addition, although a culture solution containing of organic acids or optical isomers of lactic acid present as impurity in the medium was used, the organic acids as impurity were reduced and lactic acid with high optical purity was produced.

In addition, MG1655 was obtained as ATCC47076 from American Type Culture Collection (ATCC).

EXAMPLE 2

Construction of ldhA Expression Vector and Lactic Acid-Producing Bacteria

To acquire a serine hydroxymethyltransferase (glyA) promoter, amplification was carried out with a PCR method by using Escherichia coli genome DNA as a template and SEQ ID NO: 1 and SEQ ID NO: 2 as probes, and digestion of the obtained fragment with a restriction enzyme EcoRI gave a fragment encoding a glyA promoter of about 850 bp. Furthermore, to acquire a structural gene of ldhA, amplification was carried out with a PCR method by using Escherichia coli genome DNA as a template and SEQ ID NO: 3 and SEQ ID NO: 4 as probes, and digestion of the obtained fragment with restriction enzymes EcoRI and HindIII gave an ldhA structural gene fragment of about 1.0 kbp. The above-mentioned two fragments were mixed with the fragment obtained by digestion of plasmid pUC18 using restriction enzymes EcoRI and HindIII, ligated using a DNA ligase, and then transformed to an Escherichia coli to give plasmid pGlyldhA.

The obtained plasmid pGlyldhA was transformed to an Escherichia coli MT-10934 strain to give an MT-10934/pGlyldhA strain, which is a lactic acid-producing bacteria.

In addition, pUC18 is obtained by extraction according to an established method from ATCC37253, which is available from American Type Culture Collection. Also, the MT-10934 strain has been deposited on Nov. 8, 2002 as the above-mentioned deposition number at International Patent Organism Depositary, Tsukuba Central 6, 1-1-1 Higashi, Tsukuba, Ibaraki, of National Institute of Advanced Industrial Science and Technology.

EXAMPLE 3

Production of Lactic Acid by MT-10934/pGlyldhA Strain, Lactic Acid-Producing Bacteria The MT-10934/pGlyldhA strain, which is the lactic acid-producing bacteria obtained in Example 2, was inoculated into 25 ml of LB Broth, Miller's culture solution (Difco244620) contained in a conical flask, and culture was carried out as preculture in the same manner as described in Example 1. After completing the culture, assay of the lactic acids and measurement of optical purity thereof were performed with HPLC according to an established method. The results are shown in Table 3.

TABLE 3

| Amount of D-lactic acid accumulated | 94 g/kg of culture solution |
|---|---|
| Recovered amount of culture solution | 570 g |
| Weight of dry microbial mass | 2.0 g |
| Optical purity of D-lactic acid | 99.9% ee or more |
| Amount of D-lactic acid accumulated after 50 hrs of culture initiation | 65.2 g/kg |

In the results, the reason why the total amount of lactic acid is more than the glucose amount added at culture initiation is considered to be that the carbon source in corn steep liquor was used. However, using all the reducing sugar, organic acids and amino acids in corn steep liquor, the conversion rate of 90% or more was reached.

EXAMPLE 4

Cloning of a Region Adjacent to pfl Gene of Escherichia coli

The entire base sequence of Escherichia coli genome DNA is known (GenBank accession number: U00096), and the base sequence of a gene encoding pyruvate formate-lyase of Escherichia coli(hereinafter, may be called pfl) has also been reported (GenBank accession number: AE000192). For cloning the region adjacent to the base sequence of a gene encoding pfl (2,283 bp), four kinds of oligonucleotide primers shown in SEQ ID NOS: 5, 6, 7 and 8 were synthesized. The primers of SEQ ID NOS: 6 and 7 have SphI recognition site at the 5'-terminal.

The genome DNA of the Escherichia coli MG1655 strain was prepared by the method described in Current Protocols in Molecular Biology (John Wiley & Sons). Using combinations of 1 μg of the obtained genome DNA with the primer having the base sequence of SEQ ID NO: 5 and the primer having the base sequence of SEQ ID NO: 6, and with the primer having the base sequence of SEQ ID NO: 7 and the primer having the base sequence of SEQ ID NO: 8, PCR was performed under usual conditions using 100 pmol each of the above-mentioned primer DNAs to amplify DNA fragments of about 1.8 kbp (hereinafter, may be called a pflB-L fragment) and about 1.3 kbp (hereinafter, may be called a pflB-R fragment). These DNA fragments were isolated by agarose electrophoresis, recovered, and the pflB-L fragment was digested with HindIII and SphI, and the pflB-R fragment was digested with SphI and PstI, respectively. These two kinds of digested fragments and a digest of temperature-sensitive plasmid pTH18 cs1 (GenBank accession number: AB019610) (Hashimoto-Gotoh, T., et. al., Gene, Vol. 241(1), pp 185-191 (2000)) with HindIII and PstI were reacted with T4 DNA ligase, and then the product was transformed to an *Escherichia coli* DH5α competent cell (TAKARA BIO INC.), to give a plasmid containing two fragments, i.e., a 5'-upstream adjacent fragment and a 3'-downstream adjacent fragment of a gene encoding pflB, which was designated as pTHΔpfl.

EXAMPLE 5

Preparation of pfl Gene-Disrupted Strain of *Escherichia coli* MG1655 Strain

The plasmid pTHΔpfl obtained in Example 4 was transformed to the *Escherichia coli* MG1655 strain, cultured overnight on an LB agar plate containing 10 μg/ml of chloramphenicol at 30° C., at which the cell can keep a temperature-sensitive plasmid, to give a transformant. The obtained transformant was cultured in an LB medium at 30° C. for 3 hours to overnight, and then diluted suitably with an LB liquid medium or saline, and applied onto an LB agar plate containing 10 μg/ml of chloramphenicol. This LB agar plate was cultured at 42° C., at which the temperature-sensitive plasmid can not be kept, and the grown transformant was obtained as a strain wherein the full length of the plasmid is integrated into *Escherichia coli* genome by homologous recombination between exogenome and genome.

From this strain, a genome DNA was acquired, and PCR was performed using this as a template. It was confirmed that since chloramphenicol resistant gene contained in pTH18cs1 is present on the genome and that regions homologous to each of 5'-adjacent region and 3'-adjacent region of a gene encoding pflB are present on the genome, the full length of the plasmid was a strain integrated into the *Escherichia coli* genome.

The strain in which the full length of the plasmid was integrated into *Escherichia coli* genome was inoculated to a 100 ml baffled flask containing 20 ml of an LB liquid medium without containing chloramphenicol, and this was cultured with shaking at 30° C. for 4 hours. This culture solution was suitably diluted in an LB liquid medium without containing chloramphenicol, and applied onto an LB agar medium without containing chloramphenicol. After culturing at 42° C., 96 colonies of the grown culture were randomly selected, and grown on an LB agar medium without containing chloramphenicol, and an LB agar medium containing chloramphenicol, respectively, and then chloramphenicol-sensitive strains were selected.

Furthermore, a genome DNA was acquired from the selected strains and PCR was performed using this as a template to select a strain in which a gene encoding pfl is deficient, which was designated as MG1655ΔpflB strain.

EXAMPLE 6

Production of Lactic Acid by MG1655Δpfl Strain Using Casamino Acid

A plurality of conical flasks, each containing 25 g of LB Broth, Miller's culture solution (Difco244620), were prepared as preculture. Into them, three kinds of strains, i.e., lactic acid-producing bacteria, MG1655, MG1655Δpfl strain, and MG1655Δpfl/pGlyldhA wherein the plasmid pGlyldhA as described in Example 2 was recombined with MG1655Δpfl strain according to an established method, were inoculated separately. Culture was carried out with stirring overnight at 30° C. with 120 rpm, and then the whole amount was separately inoculated into a 1 L-fermentor (BMJ-01, culture apparatus manufactured by ABLE) containing 475 g of the medium shown in Table 4. Culture was carried out under the conditions including atmospheric pressure, an aeration rate of 0.5 vvm, a stirring speed of 200 rpm, a culture temperature of 31° C., and pH of 6.7 (adjusted with NaOH) for 50 hours. After completing the culture, assay of lactic acid and measurement of optical purity thereof in the obtained culture solution were performed with HPLC according to an established method. The results are shown in Table 5.

TABLE 4

| Medium composition | |
|---|---|
| Glucose | 100 g/L |
| $Na_2HPO_4 \cdot 12H_2O$ | 6.0 g/L |
| $(NH_4)_2SO_4$ | 6.0 g/L |
| $KH_2PO_4$ | 3.0 g/L |
| NaCl | 3.0 g/L |
| $MgSO_4 \cdot 7aq$ | 0.1 g/L |
| Yeast extract | 0.5 g/L |
| Casamino acid | 5.0 g/L |

TABLE 5

| | MG1655 | MG1655Δpfl | MG1655Δpfl/ pGlyldhA |
|---|---|---|---|
| Amount of D-lactic acid accumulated | 28 g/L | 58 g/L | 63.7 g/L |

EXAMPLE 7

Production of Lactic Acid by MG1655Δpfl Using Corn Steep Liquor

MG1655, MG1655Δpfl and MG1655Δpfl/pGlyldhA were separately inoculated into 25 g of the culture solution contained in a conical flask, and culture was carried out with stirring overnight at 30° C. with 120 rpm as preculture. Then, the whole amount was separately inoculated each into a 1 L-fermentor (BMJ-01, culture apparatus manufactured by ABLE Corporation) containing 475 g of the medium shown in Table 6. Culture was carried out under the conditions including atmospheric pressure, an aeration rate of 0.5 vvm, a stirring speed of 300 rpm, a culture temperature of 35° C., and pH of 7.2 (adjusted with NaOH) for 24 hours. After completing the culture, measurements of lactic acid and the pyruvic acid in the obtained culture solution were performed with HPLC according to an established method. The results are shown in Table 7.

TABLE 6

| Medium composition | |
|---|---|
| Glucose | 10% |
| Corn steep liquor (manufactured by NIHON SHOKUHIN KAKO CO. LTD.) | 5% |
| Adecanol LG126 | 0.1% |

TABLE 7

| | MG1655 | MG1655Δpfl | MG1655Δpfl/ pGlyldhA |
|---|---|---|---|
| Amount of D-lactic acid accumulated | 52 g/L | 95 g/kg of culture solution | 95 g/kg of culture solution |
| Recovered amount of culture solution | 520 g | 560 g | 560 g |
| Weight of dry microbial mass | 2.5 g/L | 2.5 g/L | 2.5 g/L |
| Pyruvic acid | 1.1 g/L | 1.1 g/L | 0.3 g/L |
| Culture time | 24 hours | 24 hours | 24 hours |

In the results, the reason why the total amount of lactic acid is more than the glucose amount added at culture initiation is considered to be that the carbon source in corn steep liquor was used. However, using all the reducing sugar, organic acids and amino acids in corn steep liquor, the conversion rate of 90% or more was reached.

EXAMPLE 8

High Accumulation and Production of Lactic Acid by MG1655Δpfl Strain Under High Glucose Concentration MG1655Δpfl was inoculated into 25 g of the culture solution contained in a conical flask, and culture was carried out with stirring overnight with 120 rpm as preculture. Then, the whole amount was inoculated into a fermentor of BMJ-01, a culture apparatus manufactured by ABLE Corporation, containing 475 g of the medium, having the glucose concentration from 10% to 15% as shown in Table 8. Culture was carried out under the conditions including atmospheric pressure, an aeration rate of 0.5 vvm, a stirring speed of 300 rpm, a culture temperature of 35° C., and pH of 7.2 (adjusted with NaOH) until the whole glucose was depleted. After completing the culture, measurement of lactic acid was performed with HPLC according to an established method. The results are shown in Table 9.

TABLE 8

| Medium composition | |
|---|---|
| Glucose | 10%, 12%, 15% |
| Corn steep liquor (manufactured by NIHON SHOKUHIN KAKO CO. LTD.) | 5% |
| Adecanol LG126 | 0.1% |

TABLE 9

| Glucose concentration | 10% | 12% | 15% |
|---|---|---|---|
| Amount of D-lactic acid accumulated | 95 g/kg of culture solution | 112 g/kg of culture solution | 130 g/kg of culture solution |
| Recovered amount of culture solution | 560 g | 567 g | 580 g |
| Weight of dry microbial mass | 2.5 g/L | 2.5 g/L | 2.5 g/L |

The reason why the total amount of lactic acid is more than the glucose amount added at culture initiation is considered to be that the carbon source in corn steep liquor was used. However, using all the reducing sugar, organic acids and amino acids in corn steep liquor, the conversion rate of 90% or more was reached. Further, high accumulation amount of 130 g/L was attained, which had not been possible so far.

EXAMPLE 9

Investigation of the Added Amount of Corn Steep Liquor Using MG1655Δpfl Strain

MG1655Δpfl was inoculated into 25 g of the culture solution contained in a conical flask, and culture was carried out with stirring overnight with 120 rpm as preculture. Then, the whole amount was inoculated into a fermentor of BMJ-01, a culture apparatus manufactured by ABLE Corporation, containing 475 g of the medium, with the corn steep liquor concentration ranging from 1 to 10% as shown in Table 10. Culture was carried out under the conditions including atmospheric pressure, an aeration rate of 0.5 vvm, a stirring speed of 300 rpm, a culture temperature of 35° C., and pH of 7.2 (adjusted with NaOH) for 24 hours. After completing the culture, measurement of lactic acid was performed with HPLC according to an established method. The results are shown in Table 11.

TABLE 10

| Medium composition | |
|---|---|
| Glucose | 10% |
| CSL (manufactured by NIHON SHOKUHIN KAKO CO. LTD.) | 1%, 2.5%, 5%, 10% |
| Adecanol LG126 | 0.1% |

TABLE 11

| | CSL | | | |
|---|---|---|---|---|
| | 1% | 2.5% | 5% | 10% |
| Amount of D-lactic acid accumulated | 55 g/L | 90 g/L | 94 g/L | 96 g/L |

In the group where 1% corn steep liquor was added, although decrease in the production rate was observed, the production rate at 24 hours reached the amount of 55 g/L, which had not been possible so far. Further, the conversion rate of glucose used to lactic acid was maintained at 90% or more.

EXAMPLE 10

Effect of Aeration Conditions on Glycolysis Rate Using MG1655Δpfl Strain

The MG1655Δpfl strain was inoculated into 25 g of the culture solution contained in a conical flask, and culture was carried out with stirring overnight with 120 rpm as preculture. Then, the whole amount was inoculated into a fermentor of BMJ-01, a culture apparatus manufactured by ABLE Corporation, containing 475 g of the medium as shown in Table 12. Culture was carried out under conditions including atmospheric pressure and under the aeration conditions shown in Table 13 with a culture temperature of 35° C. and pH of 7.2 (adjusted with NaOH) for 24 hours. The amount of residual glucose was measured by glucose CII-test Wako (Wako Pure Chemical Industries, Ltd.).

TABLE 12

| Medium composition | |
|---|---|
| Glucose | 12% |
| CSL (manufactured by NIHON SHOKUHIN KAKO CO. LTD.) | 5% |
| Adecanol LG126 | 0.1% |

TABLE 13

| | Experimental group | | | |
|---|---|---|---|---|
| | 1 | 2 | 3 | 4 |
| Aeration rate (vvm) | 0 | 0.5 | 0.5 | 0.5 |
| Stirring speed (rpm) | 200 | 200 | 400 | 600 |

TABLE 14

| | Experimental group | | | |
|---|---|---|---|---|
| | 1 | 2 | 3 | 4 |
| Amount of residual glucose(g/L) | 59.4 | 39.4 | 21.7 | 67.9 |

It was found by this experiment that the glycolysis rate was improved according to improvement of the aeration conditions, but the glycolysis rate decreased if the aeration conditions were improved excessively.

EXAMPLE 11

Investigation of the Added Amount of Corn Steep Liquor Using MG1655Δpfl/pGlyldhA Strain MG1655ΔpflB/pGlyldhA was inoculated into 25 g of the culture solution contained in a conical flask, and culture was carried out with stirring overnight with 120 rpm as preculture. Then, the whole amount was inoculated into a fermentor of BMJ-01, a culture apparatus manufactured by ABLE Corporation, containing 475 g of the medium, with the corn steep liquor concentration ranging from 1 to 10% as shown in Table 15. Culture was carried out under the conditions including atmospheric pressure, an aeration rate of 0.5 vvm, a stirring speed 300 rpm, a culture temperature of 35° C. and pH of 7.2 (adjusted with NaOH) for 24 hours. After completing the culture, measurement of the D-lactic acid was performed with HPLC according to an established method. The results are shown in Table 16.

TABLE 15

| Medium composition | |
|---|---|
| Glucose | 10% |
| CSL (manufactured by NIHON SHOKUHIN KAKO CO. LTD.) | 1%, 2.5%, 5%, 10% |
| Adecanol LG126 | 0.1% |

TABLE 16

| | CSL | | | |
|---|---|---|---|---|
| | 1% | 2.5% | 5% | 10% |
| Amount of D-lactic acid accumulated | 58 g/L | 92 g/L | 96 g/L | 97 g/L |

The group where 1% corn steep liquor was added has the lowest productivity among the tested groups, but a production rate at 24 hours with the amount of 58 g/L is a production rate that was not possible conventionally. In addition, the conversion rate of the glucose used to the D-lactic acid was maintained at 90% or more.

EXAMPLE 12

Effect of Aeration Conditions on the Glycolysis Rate Using MG1655Δpfl/pGlyldhA Strain MG1655ΔpflB/pGlyldhA was inoculated into 25 g of the culture solution contained in a conical flask, and culture was carried out with stirring overnight with 120 rpm as preculture. Then, the whole amount was inoculated into a fermentor of BMJ-01, a culture apparatus manufactured by ABLE Corporation, containing 475 g of the medium shown in Table 17. Culture was carried out under atmospheric pressure and under the aeration conditions shown in Table 18 with a culture temperature of 35° C. and pH of 7.2 (adjusted with NaOH) for 24 hours. The amount of residual glucose was measured by glucose CII-test Wako (Wako Pure Chemical Industries, Ltd.).

TABLE 17

| Medium composition | |
|---|---|
| Glucose | 12% |
| CSL (manufactured by NIHON SHOKUHIN KAKO CO. LTD.) | 5% |
| Adecanol LG126 | 0.1% |

TABLE 18

| | Experimental group | | | |
|---|---|---|---|---|
| | 1 | 2 | 3 | 4 |
| Aeration rate (vvm) | 0 | 0.5 | 0.5 | 0.5 |
| Stirring speed (rpm) | 200 | 200 | 400 | 600 |

TABLE 19

| | Experimental group | | | |
|---|---|---|---|---|
| | 1 | 2 | 3 | 4 |
| Amount of residual glucose (g/L) | 59.4 | 36.6 | 20.1 | 54.5 |

It was found by this experiment that the glycolysis rate was improved according to improvement of the aeration conditions, but the glycolysis rate decreased if the aeration condition was improved excessively.

EXAMPLE 13

Preparation of dld Gene-Deleted *Escherichia coli*MG1655 Strain

PCR was carried out using CAACACCAAGCTTTCGCG (SEQ ID NO: 9), TTCCACTCCTTGTGGTGGC (SEQ ID NO: 10), AACTGCAGAAATTACGGATGGCAGAG (SEQ ID NO: 11) and TGTTCTAGAAAGTTCTTTGAC (SEQ ID NO: 12), which were prepared on the basis of the gene information of the region adjacent to the dld gene of MG1655 strain-derived genome DNA. The obtained fragment was digested respectively with restriction enzymes HindIII and PstI, and PstI and XbaI, to give fragments of about 1,140 bp, respectively. These fragments were mixed with the fragment which was obtained by digestion of temperature-sensitive plasmid pTH18cs1 (Hashimoto-Gotoh, T., et. al., Gene, Vol. 241(1), pp 185-191 (2000)) with HindIII and XbaI, ligated using a ligase, and then transformed to a DH5α strain at 30° C., and grown on an LB agar plate containing 10 μg/ml of chloramphenicol to give a transformant. The obtained colony was cultured in an LB liquid medium containing 10 μg/ml of chloramphenicol at 30° C. overnight, and a plasmid was recovered from the obtained microbial mass. This plasmid was transformed to MG1655 strain at 30° C., and grown on an LB agar plate containing 10 μg/ml of chloramphenicol to give a transformant. The obtained transformant was applied onto an agar plate, and cultured overnight at 30° C. Next, in order to obtain cultured microbial mass, the cultured microbial mass was applied onto an LB agar plate containing 10 μg/ml of chloramphenicol to give colonies which grow at 42° C.

Furthermore, the operation was repeated again to obtain single colonies which grow at 42° C., and a clone, in which the whole plasmid was integrated into the chromosome by homologous recombination, was selected. It was confirmed that the present clone did not have the plasmid in the cytoplasm.

Next, the above-mentioned clone was applied onto an LB agar plate, and cultured overnight at 30° C., and then inoculated into an LB liquid medium (3 ml/test tube), and cultured with shaking at 42° C. for 3 to 4 hours. This was suitably diluted (about $10^{-2}$ to $10^{-6}$) to obtain single colonies, and the diluted solution was applied onto an LB agar plate and cultured overnight at 42° C. to give colonies. From the grown colonies, 100 colonies were picked up randomly, and each of them was grown on an LB agar plate and an LB agar plate containing 10 μg/ml of chloramphenicol. Chloramphenicol-sensitive clones which grow only on an LB agar plate were selected from them. Furthermore, a fragment of about 2.0 kbp containing dld was amplified by PCR using the chromosome DNA of these desired clones, and a strain was selected in which a dld gene region was deleted. The clone which satisfies the above description was chosen as a dld-deleted strain, and the obtained strain was designated as MG1655Δdld strain.

EXAMPLE 14

Production of D-Lactic Acid by MG1655Δdld Strain

The MG1655 strain or MG1655Δdld strain was inoculated into 25 ml of LB Broth, Miller's culture solution (Difco244620) contained in a conical flask, and culture was carried out with stirring overnight with 120 rpm as preculture. The whole amount of each preculture solution was moved separately into a fermentor of BMJ-01, a culture apparatus manufactured by ABLE Corporation, containing 475 g of the medium of the composition as shown in Table 20, and culture was carried out. Culture was carried out under the conditions including atmospheric pressure, an aeration rate of 0.5 vvm, a stirring speed of 200 rpm, a culture temperature of 31° C., and pH of 6.7 (adjusted with NaOH) for 96 hours. After 48 hours and after completing the culture, assay of lactic acid, pyruvic acid, formic acid and acetic acid was performed with HPLC according to an established method. The results after 48 hours are shown in Table 21, and the results after completing the culture are shown in Table 22, in which MG1655 strain and MG1655Δdld strain are represented by Wild and Δdld, respectively.

TABLE 20

| Medium composition | |
|---|---|
| Glucose | 100 g/L |
| $Na_2HPO_4 \cdot 12H_2O$ | 6.0 g/L |
| $(NH_4)_2SO_4$ | 6.0 g/L |
| $KH_2PO_4$ | 3.0 g/L |
| NaCl | 3.0 g/L |
| $MgSO_4 \cdot 7aq$ | 0.1 g/L |
| Yeast extract | 0.5 g/L |
| Casamino acid | 5.0 g/L |

TABLE 21

| Results after 48 hours | | |
|---|---|---|
| | Wild | Δdld |
| Amount of D-lactic acid accumulated | 26 g/L | 22 g/L |
| Amount of pyruvic acid accumulated | 4.5 g/L | 1.1 g/L |
| Amount of formic acid accumulated | 5.0 g/L | 1.55 g/L |
| Amount of acetic acid accumulated | 14 g/L | 9.5 g/L |

TABLE 22

| Results after 96 hours | | |
|---|---|---|
| | Wild | Δdld |
| Amount of D-lactic acid accumulated | 36 g/L | 41 g/L |
| Amount of pyruvic acid accumulated | 5.84 g/L | 1.26 g/L |
| Amount of formic acid accumulated | 3.4 g/L | 0 g/L |
| Amount of acetic acid accumulated | 12 g/L | 11 g/L |

EXAMPLE 15

Preparation of pfl and dld Gene-Deleted *Escherichia coli* MG1655 Strain

The plasmid pTHΔpfl obtained in Example 4 was transformed to MG1655Δdld strain, and grown on an LB agar plate containing 10 μg/ml of chloramphenicol to give a transformant. The obtained transformant was applied onto an agar plate, and cultured overnight at 30° C. Next, in order to obtain cultured microbial mass, the cultured transformant was applied onto an LB agar plate containing 10 μg/ml of chloramphenicol to give colonies which grow at 42° C.

By treating the obtained clone in the same manner as in Example 5, dld and pfl gene-deleted MG1655 strain was acquired, and was designated as MG1655ΔpflΔdld strain.

EXAMPLE 16

Introduction of ldhA Expression Vector to MG1655Δdld Strain and MG1655ΔpflΔdld Strain The plasmid pGlyldhA obtained in Example 2 was transformed to MG1655Δdld strain and MG1655ΔpflΔdld strain, respectively, to give MG1655Δdld/pGlyldhA strain and MG1655ΔpflΔdld/pGlyldhA strain.

EXAMPLE 17

Production of D-Lactic Acid by MG1655 Strain MG1655Δdld strain, MG1655Δpfl strain, MG1655ΔpflΔdld strain, MG1655Δdld/pGlyldhA Strain and MG1655ΔpflΔdld/pGlyldhA Strain MG1655 strain, MG1655Δdld strain, MG1655Δpfl strain, MG1655ΔpflΔdld strain, MG1655Δdld/pGlyldhA strain and MG1655ΔpflΔdld/pGlyldhA strain were separately inoculated each into 25 ml of LB Broth, Miller's culture solution contained in a conical flask, and culture was carried out with stirring overnight with 120 rpm as preculture. The whole amount of each preculture solution was moved separately into a fermentor of BMJ-01, a culture apparatus manufactured by ABLE Corporation, containing 475 g of the medium of the composition as shown in Table 20, and culture was carried out. Culture was carried out under the conditions including atmospheric pressure, an aeration rate of 0.5 vvm, a stirring speed of 200 rpm, a culture temperature of 31° C., and pH of 6.7 (adjusted with NaOH) for 96 hours. After completing the culture, assay of lactic acid, pyruvic acid, formic acid and acetic acid was performed with HPLC according to an established method. The results after 96 hours are shown in Table 23. The strain names are represented by A, B, C, D, E, and F, respectively.

TABLE 23

Concentrations of various organic acids in the culture solution
(Unit of the numeric value in Table is all in g/L)

|  | A | B | C | D | E | F |
|---|---|---|---|---|---|---|
| Amount of D-lactic acid accumulated | 40 | 41.5 | 60 | 61 | 43 | 65 |
| Amount of pyruvic acid accumulated | 2.7 | 1.0 | 2.3 | 1.1 | 0.9 | 0.7 |
| Amount of formic acid accumulated | 4.0 | 3.5 | ND | ND | 3.5 | ND |
| Amount of acetic acid accumulated | 11 | 7.3 | 4.4 | 4.3 | 7.0 | 4.2 |

EXAMPLE 18

Construction of ldhA Expression Vector and a Transformant of ldhA Expression Vector Under Control of GAPDH Promoter The base sequence of the *Escherichia coli* ldhA gene has been already reported (GenBank accession number: U36928). To acquire a glyceraldehyde-3-phophate dehydrogenase (GAPDH) promoter, AACGAATTCTCGCAATGATTGACACGATTC (SEQ ID NO: 13) and ACAGAATTCGCTATTTGTTAGTGAATAAAAGG (SEQ ID NO: 14) were amplified with a PCR method using the genome DNA of *Escherichia coli* MG1655 strain as a template. The obtained DNA fragment was digested with a restriction enzyme EcoRI to give a fragment of about 100 bp, which encodes a GAPDH promoter. Furthermore, to acquire a structural gene of D-lactate dehydrogenase (ldhA), GGAATTCCGGAGAAAGTCTTATGAAACT (SEQ ID NO: 15) and CCCAAGCTTTTAAACCAGTTCGTTCGGGC (SEQ ID NO: 16) were amplified with a PCR method using the genome DNA of *Escherichia coli* MG1655 strain as a template. The obtained DNA fragment was digested with restriction enzymes EcoRI and HindIII to give D-lactate dehydrogenase (ldh) fragment of about 1.0 kbp. Two DNA fragments mentioned above were mixed with the fragment obtained with digestion of plasmid pUC18 using restriction enzymes EcoRI and HindIII, ligated using a ligase, and then transformed to an *Escherichia coli* DH5α competent cell (manufactured by TAKARA BIO INC.), to give a transformant which grows on an LB agar plate containing 50 μg/mL of ampicillin. The obtained colony was cultured in an LB liquid medium containing 50 μg/mL of ampicillin and on the LB medium at 30° C. overnight, and the plasmid pGAPldhA was recovered from the obtained microbial mass. This plasmid pGAPldhA was transformed to MG1655ΔpflΔdld strain, and cultured on an LB agar plate containing 1 μg/mL of ampicillin at 37° C. overnight to give MG1655ΔpflΔdld/pGAPldhA strain.

EXAMPLE 19

Substitution of the ldhA Promoter on the Genome of *Escherichia coli* MG1655ΔpflΔdld Strain with GAPDH Promoter The entire base sequence of the *Escherichia coli* genome DNA is known (GenBank accession number: U00096), and the base sequence of the *Escherichia coli* ldhA gene has also been reported (GenBank accession number: U36928). PCR was performed using AAGGTACCACCAGAGCGTTCTCAAGC (SEQ ID NO: 17) and GCTCTAGATTCTCCAGTGATGTTGAATCAC (SEQ ID NO: 18), which were prepared on the basis of the gene information of 5'-adjacent region of the *Escherichia coli* MG1655 strain-derived ldhA gene, using *Escherichia coli* genome DNA as a template, to amplify a DNA fragment of about 1000 bp.

In addition, PCR was performed using GGTCTAGAGCAATGATTCACACGATTCG (SEQ ID NO: 19), which was prepared on the basis of the sequence information of the glyceraldehyde-3-phophate dehydrogenase (GAPDH) promoter of *Escherichia coli* MG1655 strain, and AACTGCAGGTTCGTTCTCATACACGTCC (SEQ ID NO: 20), which was prepared on the basis of the sequence information of the ldhA gene of *Escherichia coli* MG1655 strain, using the expression vector pGAPldhA prepared in Example 18 as a template, to give a DNA fragment of about 850 bp which contains a GAPDH promoter and an initiation codon-adjacent region of the ldhA gene.

The fragment obtained above was digested with restriction enzymes KpnI and XbaI, and XbaI and PstI, respectively, and this fragment was mixed with the fragment obtained by digestion of temperature-sensitive plasmid pTH18cs1 with KpnI and PstI, ligated using a ligase, and then transformed to a DH5α competent cell (manufactured by TAKARA BIO INC.) at 30° C., to give a transformant which grows on an LB agar plate containing 10 μg/ml of chloramphenicol. The obtained colony was cultured in an LB liquid medium containing 10 μg/ml of chloramphenicol at 30° C. overnight, the plasmid was recovered from the obtained microbial mass, which was designated as pTH-GAPldhA. pTH-GAPldhA was transformed to MG1655ΔpflΔdld strain at 30° C., cultured in an LB agar plate containing 10 μg/ml of chloramphenicol at 30° C. overnight, to give a transformant. The obtained transformant was inoculated into an LB liquid medium containing 10 μg/ml of chloramphenicol, and cultured overnight at 30° C. Next, in order to obtain cultured microbial mass, the cultured transformant was applied onto an LB agar plate containing 10 μg/ml of chloramphenicol to give colonies which grow at 42° C. The obtained colonies were cultured in an LB liquid medium without containing a drug at 30° C. overnight, and further applied onto an LB agar plate without containing a drug to give colonies which grow at 42° C.

From the grown colonies, 100 colonies were picked up randomly, and each of them was grown on an LB agar plate without containing a drug and an LB agar plate containing 10 μg/ml of chloramphenicol, to select chloramphenicol-sensitive clones. Furthermore, a fragment of about 800 bp containing a GAPDH promoter and an ldhA gene was amplified by PCR using the chromosome DNA of these desired clones, to select a strain in which the ldhA promoter region is substituted with the GAPDH promoter, and the clone which satisfies the above description was designated as MG1655ΔpflΔdld/GAPldhA genome-inserted strain.

EXAMPLE 20

Production of D-Lactic Acid by MG1655ΔpflΔdld Strain, MG1655ΔpflΔdld/pGAPldhA Strain and MG1655ΔpflΔdld/GAPldhA Genome-Inserted Strain MG1655ΔpflΔdld strain, MG1655ΔpflΔdld/pGAPldhA strain and MG1655ΔpflΔdld&pflB/GAPldhA genome-inserted strain were separately inoculated each into 25 mL of LB Broth, Miller's culture solution (Difco244620) contained in a conical flask, and culture was carried out with stirring overnight with 120 rpm as preculture. The whole amount of each preculture solution was moved into a 1 L-fermentor (BMJ-01, culture apparatus manufactured by ABLE Corporation), containing 475 g of a medium containing 120 g/L of glucose and 5% corn steep liquor (manufactured by NIHON SHOKUHIN KAKO CO. LTD.), and culture was carried out. Culture was carried out under the conditions including atmospheric pressure, an aeration rate of 0.5 vvm, a stirring speed of 200 rpm, a culture temperature of 35° C., and pH of 7.2 (adjusted with NaOH) until glucose was depleted. After completing the culture, the amount of D-lactic acid accumulated in the obtained culture solution was measured with HPLC according to an established method. The results are shown in FIG. 1. The accumulation and production of D-lactic acid was 109.0 g/L for MG1655ΔpflΔdld strain 48 hours, 115.6 g/L for MG1655ΔpflΔdld/pGAPldhA strain 48 hours and 113.5 g/L for MG1655ΔpflΔdld/GAPldhA genome-inserted strain 30 hours, respectively.

EXAMPLE 21

Preparation of *Escherichia coli* MG1655ΔpflΔdldΔmdh Strain

The entire base sequence of *Escherichia coli* genome DNA is known (GenBank accession number: U00096), and the base sequence of the *Escherichia coli* mdh gene has also been reported (GenBank accession number: AE000403). For cloning the region adjacent to the base sequence of a gene encoding mdh (939 bp), four kinds of oligonucleotide primers shown in SEQ ID NOS: 21, 22, 23 and 24 were synthesized. The primer having the base sequence of SEQ ID NO: 21 has a KpnI recognition site at the 5'-terminal, the primers having the base sequences of SEQ ID NOS: 22 and 23 have a BamHI recognition site at the 5'-terminal, the primer having the base sequence of SEQ ID NO: 24 has a XbaI recognition site at the 5'-terminal, respectively.

The genome DNA of *Escherichia coli* MG1655 strain was prepared according to the method described in Current Protocols in Molecular Biology (JohnWiley & Sons). Using combinations of 1 μg of the obtained genome DNA with SEQ ID NO: 21 and SEQ ID NO: 22, and with SEQ ID NO: 23 and SEQ ID NO: 24, PCR was performed using 100 pmol each of the above-mentioned primer DNAs under usual conditions to amplify DNA fragments of about 800 bp (hereinafter, may be called an mdh-L fragment) and about 1000 bp (hereinafter, may be called an mdh-R fragment). These DNA fragments were isolated by agarose electrophoresis, recovered, and the mdh-L fragment was digested with KpnI and BamHI and the mdh-R fragment was digested with BamHI and XbaI, respectively. These two kinds of digested fragments and a digest of the temperature-sensitive plasmid pTH18cs1 (GenBank accession number: AB019610) (Hashimoto-Gotoh, T., et. al., Gene, Vol. 241(1), pp 185-191 (2000)) with KpnI and XbaI were reacted with T4 DNA ligase, and then transformed to an *Escherichia coli* DH5α competent cell (TAKARA BIO INC.), to give a plasmid containing two fragments, i.e., a 5'-upstream adjacent fragment and a 3'-downstream adjacent fragment of a gene encoding mdh, and the present plasmid was designated as pTHΔmdh.

The plasmid pTHΔmdh was transformed to an *Escherichia coli* MG1655ΔpflΔdld strain, and mdh gene-disrupted MG1655ΔpflΔdld strain was acquired in the same manner as in Example 5. The present strain was designated as MG1655ΔpflΔdldΔmdh strain.

COMPARATIVE EXAMPLE 1

Preparation of *Escherichia coli* MG1655ΔpflBΔdldΔppc Strain

The entire base sequence of *Escherichia coli* genome DNA is known (GenBank accession number: U00096), and the base sequence of the *Escherichia coli* ppc gene has also been reported (GenBank accession number: AE000469). For cloning the region adjacent to the base sequence of a gene encoding ppc (2,652 bp), four kinds of oligonucleotide primers which have base sequences shown in SEQ ID NOS: 25, 26, 27 and 28 were synthesized. The primers of SEQ ID NOS: 26 and 27 have an XbaI recognition site at the 5'-terminal, and the primer of SEQ ID NO: 28 has a SacI recognition site at the 5'-terminal respectively.

Using combinations of 1 μg of the genome DNA of *Escherichia coli* MG1655 strain with SEQ ID NO: 25 and SEQ ID NO: 26, and with SEQ ID NO: 27 and SEQ ID NO: 28, PCR was performed using 100 pmol each of the above-mentioned primer DNAs under usual conditions to amplify DNA fragments of about 1,450 bp (hereinafter, may be called a ppc-L fragment) and about 750 bp (hereinafter, may be called a ppc-R fragment). These DNA fragments were isolated by agarose electrophoresis, recovered, and the ppc-L fragment was digested with HindIII and XbaI and the ppc-R fragment was digested with XbaI and SacI, respectively.

These two kinds of digested fragments and a digest of the temperature-sensitive plasmid pTH18cs1 with HindIII and SacI were reacted with T4 DNA ligase, and then transformed to an *Escherichia coli* DH5α competent cell (TAKARA BIO INC.), to give a plasmid containing two fragments, i.e., a 5'-upstream adjacent fragment and a 3'-downstream adjacent fragment of a gene encoding ppc, and this plasmid was designated as pTHΔppc.

The plasmid pTHΔppc was transformed to an *Escherichia coli* MG1655ΔpflΔdld strain, and finally ppc gene-disrupted MG1655ΔpflΔdld strain was acquired. The present strain was designated as MG1655ΔpflBΔdldΔppc strain. In addition, details of the method for obtaining the present strain were in accordance with the method described in Example 5.

COMPARATIVE EXAMPLE 2

Preparation of *Escherichia coli* MG1655ΔpflΔdldΔfrd Strain

The entire base sequence of *Escherichia coli* genome DNA is known (GenBank accession number: U00096), and the base sequence of the *Escherichia coli* frd gene has also been reported (GenBank accession number: AE000487). The frd gene, which is attempted for deletion in the present Example, is a gene which contains four kinds of genes, i.e., a gene encoding frdA (1,809 bp), a gene encoding frdB (735 bp), a gene encoding frdC (396 bp) and a gene encoding frdD (360 bp). For cloning the region adjacent to the base sequence of the frd gene, four kinds of oligonucleotide primers which have the base sequences shown in SEQ ID NOS: 29, 30, 31 and 32 were synthesized. The primer of SEQ ID NO: 29 has an EcoRI recognition site at the 5'-terminal, the primers of SEQ ID NOS: 30 and 31 have a BamHI recognition site at the 5'-terminal, and the primer of SEQ ID NO: 32 has a HindIII recognition site inside thereof, respectively.

Using combinations of 1 µg of the genome DNA of *Escherichia coli* MG1655 strain with SEQ ID NO: 29 and SEQ ID NO: 30, and with SEQ ID NO: 31 and SEQ ID NO: 32, PCR was performed using 100 pmol each of the above-mentioned primer DNAs under usual conditions to amplify DNA fragments of about 600 bp (hereinafter, may be called a frd-L fragment) and about 800 bp (hereinafter, may be called a frd-R fragment). These DNA fragments were isolated by agarose electrophoresis, recovered. Subsequently, the frd-L fragment was digested with EcoRI and BamHI and the frd-R fragment was digested with BamHI and HindIII, respectively. These two kinds of digested fragments and a digest of the temperature-sensitive plasmid pTH18cs1 with EcoRI and HindIII were reacted with T4 DNA ligase, and then transformed to an *Escherichia coli* DH5 competent cell (TAKARA BIO INC.), to give a plasmid containing two fragments, i.e., a 5'-upstream adjacent fragment and a 3'-downstream adjacent fragment of a gene encoding frd, and this plasmid was designated as pTHΔfrd.

The plasmid pTHΔfrd was transformed to an *Escherichia coli* MG1655Δpflδdld strain, and finally frd gene-disrupted MG1655ΔpflΔdld strain was obtained, which was designated as MG1655ΔpflΔdldΔfrd strain. Details of the method for obtaining the present strain were in accordance with the method described in Example 5.

EXAMPLE 22

Preparation of *Escherichia coli* MG1655ΔpflΔdldΔmdhΔasp Strain

The entire base sequence of *Escherichia coli* genome DNA is known (GenBank accession number: U00096), and the base sequence of the *Escherichia coli* aspA gene has also been reported (GenBank accession number: AE000486). For cloning the region adjacent to the base sequence of a gene encoding aspA (1,482 bp), four kinds of oligonucleotide primers shown in SEQ ID NO: 33, 34, 35 and 36 were synthesized.

Using combinations of 1 µg of the genome DNA of *Escherichia coli* MG1655 strain with SEQ ID NO: 33 and SEQ ID NO: 34, and with SEQ ID NO: 35 and SEQ ID NO: 36, PCR was performed using 100 pmol each of the above-mentioned primer DNAs under usual conditions to amplify DNA fragments of about 910 bp (hereinafter, may be called an aspA-L fragment) and about 1,100 bp (hereinafter, may be called an aspA-R fragment). These DNA fragments were isolated by agarose electrophoresis and recovered. Both of AspA-L fragment and the AspA-R fragment were smoothed at end portion with a DNA Blunting Kit (TAKARA BIO INC.), and then 5'-terminal was phosphorylated using T4 polynucleotide kinase according to an established method. On the other hand, temperature-sensitive plasmid pTH18cs1 was digested with SmaI, and then dephosphorylation was carried out by alkaline phosphatase. Two kinds of the phosphorylated fragments and the dephosphorylated plasmid were reacted with T4 DNA ligase, and then transformed to an *Escherichia coli* DH5α competent cell (TAKARA BIO INC.), to give a plasmid containing two fragments, i.e., a 5'-upstream adjacent fragment and a 3'-downstream adjacent fragment of a gene encoding aspA, and this plasmid was designated as pTHΔasp.

The plasmid pTHΔasp was transformed to an *Escherichia coli* MG1655ΔpflΔdldΔmdh strain, and finally aspA gene-disrupted MG1655ΔpflΔdldΔmdh strain was obtained, which was designated as MG1655ΔpflΔdldΔmdhΔasp strain. Details of the method for obtaining the present strain were in accordance with the method described in Example 5.

EXAMPLE 23

Preparation of *Escherichia coli* MG1655ΔpflΔdldΔmdhΔasp strain/GAPldhA genome-inserted strain The plasmid pTH-GAPldhA obtained in Example 19 was transformed to an *Escherichia coli* MG1655ΔpflΔdldΔmdhΔasp strain at 30° C., cultured in an LB agar plate containing 10 µg/ml of chloramphenicol at 30° C. overnight, to give a transformant. The obtained transformant was inoculated into an LB liquid medium containing 10 µg/ml of chloramphenicol, and cultured overnight at 30° C. Next, in order to obtain cultured microbial mass, the cultured transformant was applied onto an LB agar plate containing 10 µg/ml of chloramphenicol to give colonies which grow at 42° C. The obtained colonies were cultured in an LB liquid medium without containing a drug at 30° C. overnight, and further applied onto an LB agar plate without containing a drug to give colonies which grow at 42° C.

From the grown colonies, 100 colonies were picked up randomly, and each of them was grown on an LB agar plate without containing a drug and an LB agar plate containing 10 µg/ml of chloramphenicol, to select chloramphenicol-sensitive clones. Furthermore, a fragment of about 800 bp containing GAPDH promoter and ldhA gene were amplified by PCR using the chromosome DNA of these desired clones, to select a strain in which the ldhA promoter region is substituted with the GAPDH promoter, and the clone which satisfies the above description was designated as MG1655ΔpflΔdldΔmdhΔasp/ GAPldhA genome-inserted strain.

EXAMPLE 24

Figure 2:
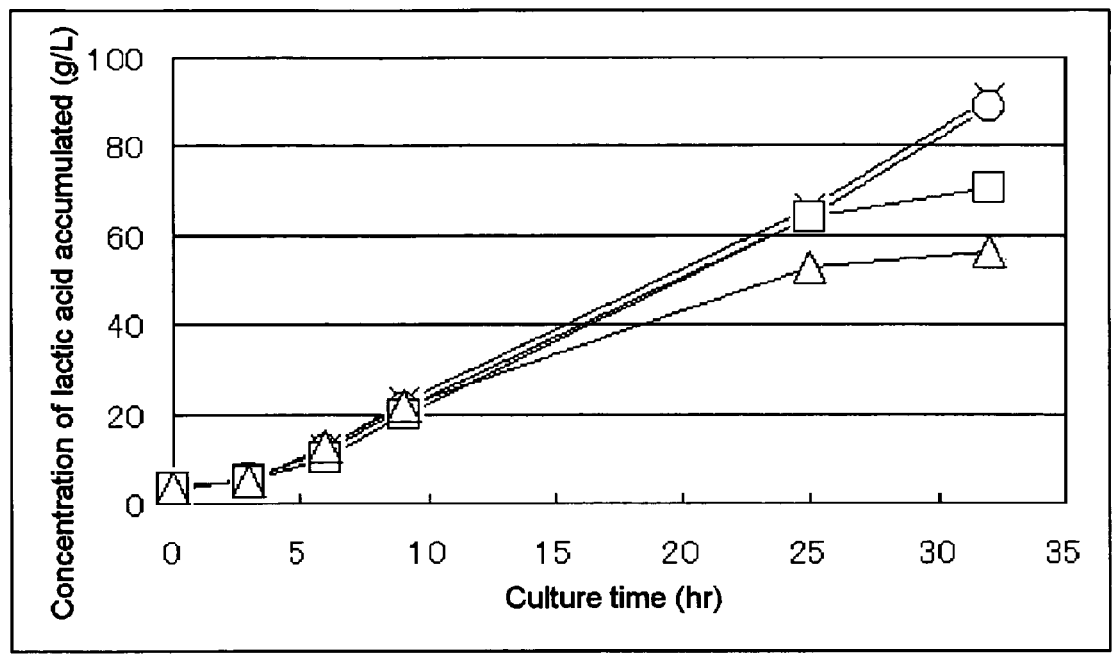
FIG. 2 is a graph which shows the time course of the concentration of lactic acid accumulated in the culture solution in Example 24. In the figure, the cross shows the results of the ΔpflΔdld strain, the circle shows the results of the ΔpflΔdldΔmdh strain, the triangle shows the results of the ΔpflΔdldΔppc strain, and the square shows the results of the ΔpflΔdldΔfrd strain.
Figure 3:
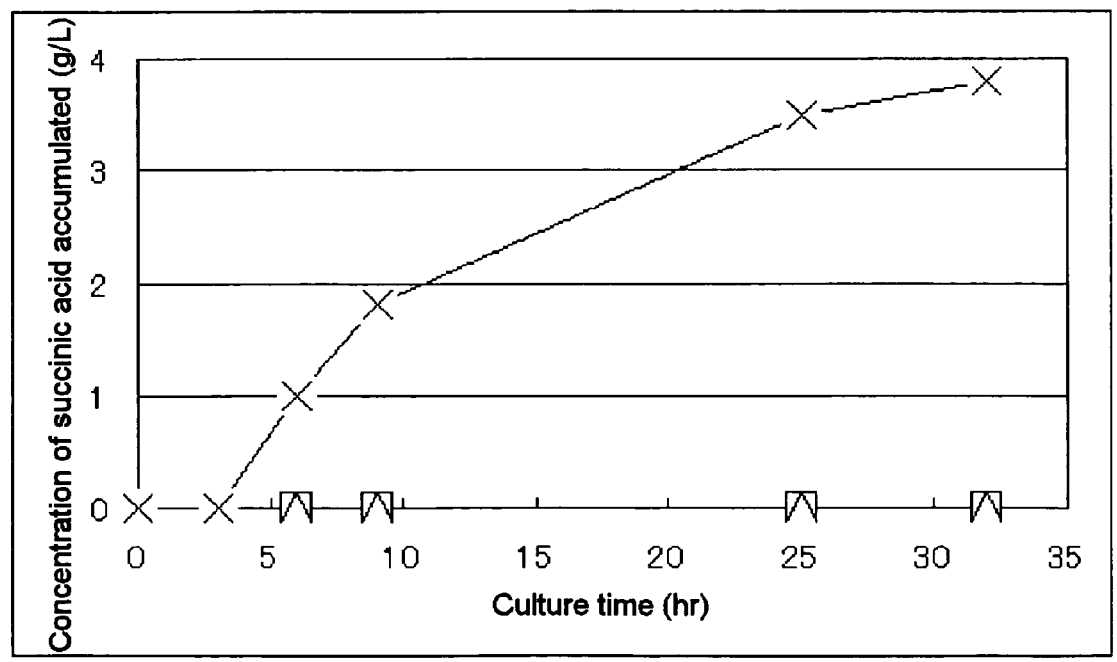
FIG. 3 is a graph which shows the time course of the concentration of succinic acid accumulated in the culture solution in Example 24. In the figure, the cross shows the results of the ΔpflΔdld strain, the circle shows the results of the ΔpflΔdldΔmdh strain, the triangle shows the results of the ΔpflΔdldΔppc strain, and the square shows the results of the ΔpflΔdldΔfrd strain.

Production of D-lactic Acid and Succinic Acid Using Escherichia coli MG1655ΔpflΔdldΔmdh Strain Escherichia coli MG1655ΔpflΔdld strain obtained in Example 15, Escherichia coli MG1655ΔpflΔdldΔmdh strain obtained in Example 21, Escherichia coli MG1655ΔpflΔdldΔppc strain obtained in Comparative example 1 and Escherichia coli MG1655ΔpflΔdldΔfrd strain obtained in Comparative example 2 were separately inoculated into four conical flasks each containing 25 ml of LB Broth, Miller's culture solution (Difco244620), and culture was carried out with stirring overnight at 30° C. with 120 rpm as preculture. Then, the whole amount of the above-mentioned flask content was separately inoculated into four 1 L volume fermentors (BMJ-01, culture apparatus manufactured by ABLE Corporation), each containing 475 g of the medium shown in Table 24. Culture was carried out under the conditions including atmospheric pressure, an aeration rate of 0.5 vvm, a stirring speed of 200 rpm, a culture temperature of 35° C., and pH of 7.2 (adjusted with NaOH) for 32 hours. After completing the culture, concentrations of lactic acid and succinic acid in the obtained culture solution were measured with HPLC according to an established method. The results of lactic acid accumulation are shown in FIG. 2, and the results of succinic acid accumulation are shown in FIG. 3.

For lactic acid, accumulation using ΔpflΔdldΔmdh strain showed 89 g/L at 32 hours, and showed the same accumulation as ΔpflΔdld strain, while accumulation using ΔpflΔdldΔppc strain and ΔpflΔdldΔfrd strain showed 56 g/L and 71 g/L, respectively.

For succinic acid, accumulation using ΔpflΔdld strain showed 3.8 g/L at 32 hours, while the remaining three strains showed no accumulation.

TABLE 24

| Medium composition | |
|---|---|
| Glucose | 12% |
| Corn steep liquor (manufactured by NIHON SHOKUHIN KAKO CO. LTD.) | 5% |

(Residual: Water)

EXAMPLE 25

Figure 4:
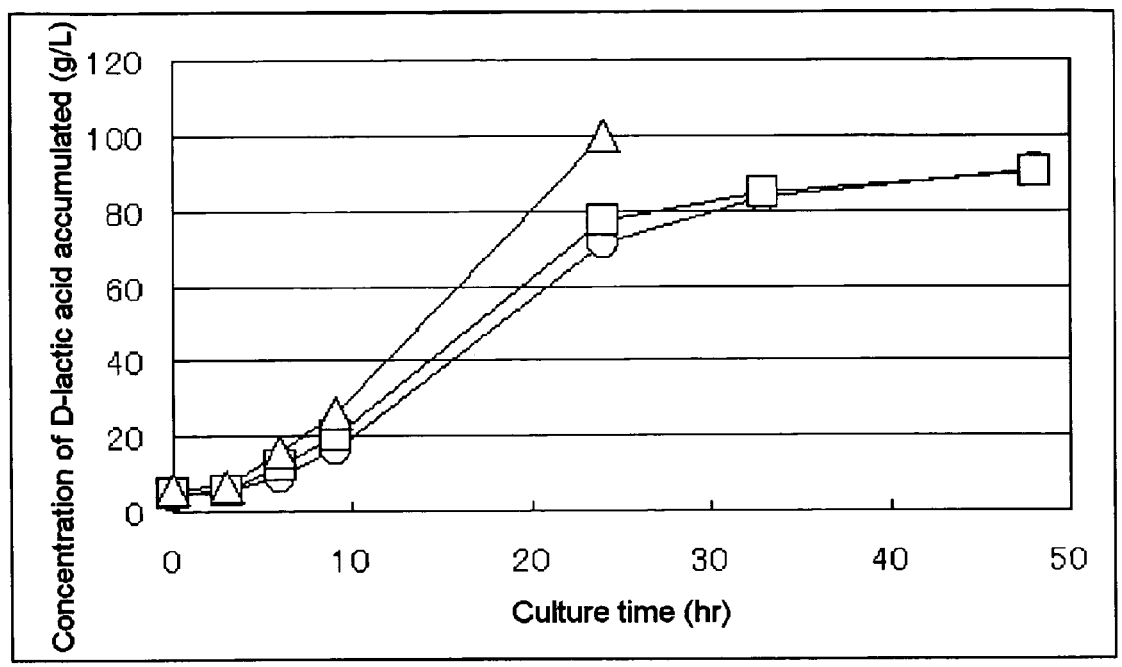
FIG. 4 is a graph which shows the time course of the concentration of lactic acid accumulated in the culture solution in Example 25. In the figure, the circle shows the results of the ΔpflΔdldΔmdhΔasp strain, the triangle shows the results of the ΔpflΔdldΔmdhΔasp/GAPldhA genome-inserted strain, and the square shows the results of the ΔpflΔdldΔmdh strain.
Figure 5:
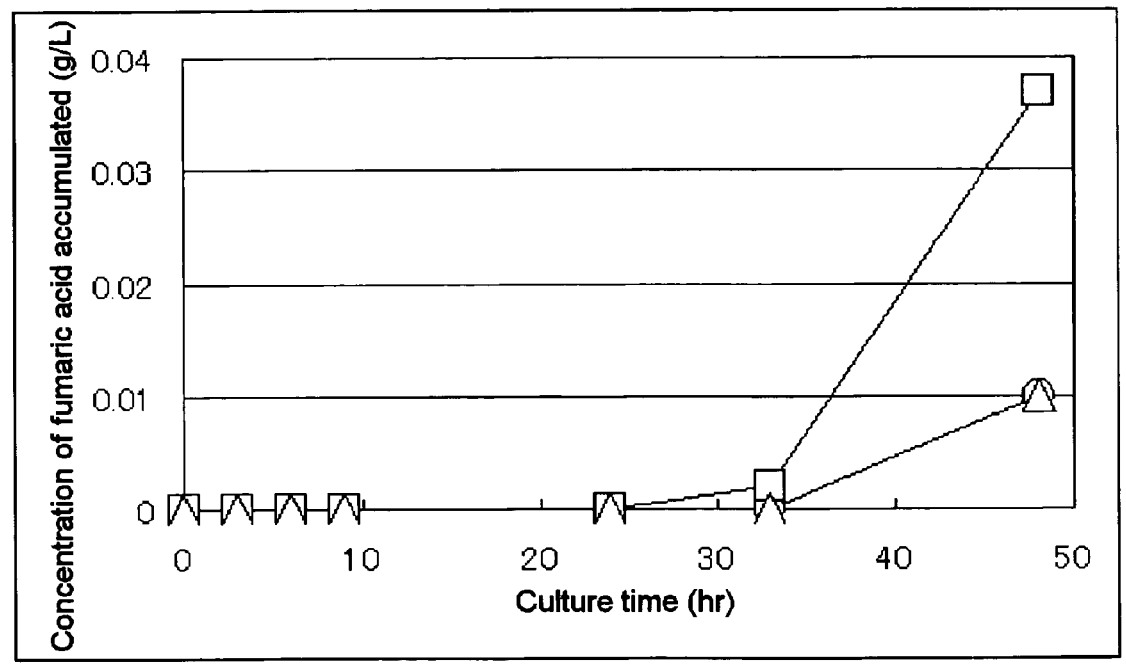
FIG. 5 is a graph which shows the time course of fumaric acid accumulation concentration in the culture solution in Example 25. In the figure, the circle shows the results of ΔpflΔdldΔmdhΔasp strain, the triangle shows the results of ΔpflΔdldΔmdhΔasp/GAPldhA genome-inserted strain, and the square shows the results of ΔpflΔdldΔmdh strain.

Production of D-lactic acid and Fumaric Acid by Escherichia coli MG1655ΔpflΔdldΔmdhΔasp Strain and MG1655ΔpflΔdldΔmdhΔasp/GAPldhA Genome-Inserted Strain Escherichia coli MG1655ΔpflΔdldΔmdhΔasp strain obtained in Example 22, Escherichia coli MG1655ΔpflΔdldΔmdhΔasp/GAPldhA genome-inserted strain obtained in Example 23 and ΔpflΔdldΔmdh strain obtained in Example 21 were separately inoculated into three conical flasks each containing 25 ml of LB Broth, Miller's culture solution (Difco244620), and culture was carried out with stirring overnight at 30° C. with 120 rpm as preculture. Then, the whole amount of the above-mentioned flask content was separately inoculated into three 1 L volume fermentors (BMJ-01, culture apparatus manufactured by ABLE Corporation), each containing 475 g of the medium shown in Table 24. Culture was carried out under the conditions including atmospheric pressure, an aeration rate of 0.5 vvm, a stirring speed of 200 rpm, a culture temperature of 35° C., and pH of 7.2 (adjusted with NaOH) for 48 hours. After completing the culture, concentrations of lactic acid and fumaric acid in the obtained culture solution were measured with HPLC according to an established method. The results of lactic acid accumulation are shown in FIG. 4, and the results of fumaric acid accumulation are shown in FIG. 5.

For lactic acid, accumulation using ΔpflΔdldΔmdhΔasp strain showed 91 g/L at 48 hours and ΔpflΔdldΔmdh strain showed a similar accumulation of 90 g/L at 48 hours, while ΔpflΔdldΔmdhΔasp/GAPldhA genome-inserted strain showed 98 g/L accumulation at 24 hours.

For fumaric acid, accumulation using ΔpflΔdldΔmdh strain showed 0.037 g/L at 48 hours, whereas accumulation using ΔpflΔdldΔmdhΔasp strain and ΔpflΔdldΔmdhΔasp/GAPldhA genome-inserted strain showed 0.01 g/L at 48 hours.

---

The invention claimed is:

1. A genetically-engineered *Escherichia coli* comprising:
a gene encoding an NADH-dependent D-lactate dehydrogenase (ldhA) obtained from *Escherichia coli*,
a disruption in said *Escherichia coli* of an endogenous FAD-dependent D-lactate dehydrogenase (dld) gene resulting in inactivation or reduction of its inherent activity, and
a disruption in said *Escherichia coli* of an endogenous pyruvate formate-lyase (pfl) gene resulting in inactivation or reduction of its inherent activity,
wherein said ldhA gene is integrated in the genome of said *Escherichia coli* and said ldhA gene product is expressed under the control of an *Escherichia coli* promoter that is not a promoter of the ldhA gene, and wherein said genetically-engineered *Escherichia coli* produces at least 113.5 g/L D-lactic acid at 30 hours when cultured.

2. The genetically-engineered *Escherichia coli* according to claim 1, wherein said ldhA gene expresses the ldhA in the genome of the *Escherichia coli* by using a promoter of a gene which controls expression of a protein involved in a glycolytic pathway, a nucleic acid biosynthesis pathway, or an amino acid biosynthesis pathway.

3. The genetically-engineered *Escherichia coli* according to claim 2, wherein said promoter that controls expression of the protein involved in the glycolytic pathway, the nucleic acid biosynthesis pathway, or the amino acid biosynthesis pathway is a promoter of a glyceraldehyde-3-phosphate dehydrogenase gene obtained from *Escherichia coli*.

4. A genetically-engineered *Escherichia coli* comprising:
a gene encoding an NADH-dependent D-lactate dehydrogenase (ldhA) obtained from *Escherichia coli*,
a disruption in said *Escherichia coli* of an endogenous FAD-dependent D-lactate dehydrogenase (dld) gene resulting in inactivation or reduction of its inherent activity,
a disruption in said *Escherichia coli* of an endogenous pyruvate formate-lyase (pfl) gene resulting in inactivation or reduction of its inherent activity,
a disruption in said *Escherichia coli* of an endogenous malate dehydrogenase (mdh) gene resulting in inactivation or reduction of its inherent activity, and
a disruption in said *Escherichia coli* of an endogenous aspartate ammonia-lyase (aspA) gene resulting in inactivation or reduction of its inherent activity,
wherein said ldhA gene is integrated in the genome of said *Escherichia coli* and said ldhA gene product is expressed under the control of an *Escherichia coli* promoter that is not a promoter of the ldhA gene, and wherein said genetically-engineered *Escherichia coli* produces at least 98 g/L D-lactic acid at 30 hours when cultured.

5. A method for producing D-lactic acid, which comprises culturing the microorganism according to claim 1 in a liquid medium, wherein D-lactic acid is produced, accumulated, and isolated from the liquid medium.

6. A method for producing D-lactic acid, which comprises culturing the microorganism according to claim 4 in a liquid medium, wherein D-lactic acid is produced, accumulated, and isolated from the liquid medium.

7. The method for producing D-lactic acid according to claim 5, wherein culture is carried out on a medium to which two or more kinds of amino acids are added.

8. The method for producing D-lactic acid according to claim 6, wherein culture is carried out on a medium to which two or more kinds of amino acids are added.

9. The method for producing lactic acid according to claim 5, wherein culture is carried out under aerobic conditions.

10. The method for producing lactic acid according to claim 6, wherein culture is carried out under aerobic conditions.

11. The method for producing lactic acid according to claim 9, wherein the aerobic conditions enable supply of oxygen which satisfies a requirement of an oxygen-transfer coefficient $K_L a$ of not less than 1 $h^{-1}$ and not more than 400 $h^{-1}$ at normal pressure using water at a temperature of 30° C.

12. The method for producing lactic acid according to claim 10, wherein the aerobic conditions enable supply of oxygen which satisfies a requirement of an oxygen-transfer coefficient $K_L a$ of not less than 1 $h^{-1}$ and not more than 400 $h^{-1}$ at normal pressure using water at a temperature of 30° C.

13. The method for producing lactic acid according to claim 5, wherein the culture pH is 6 to 8.

14. The method for producing lactic acid according to claim 6, wherein the culture pH is 6 to 8.

15. The genetically-engineered *Escherichia coli* of claim 1, wherein said promoter is a serine hydroxymethyltransferase (glyA) promoter.

16. The genetically-engineered *Escherichia coli* of claim 1, wherein said promoter is a glyceraldehyde-3-phosphate dehydrogenase (GAPDH) promoter.

17. A genetically-engineered *Escherichia coli* comprising:
a gene encoding an NADH-dependent D-lactate dehydrogenase (ldhA) obtained from *Escherichia coli*,
a disruption in said *Escherichia coli* of an endogenous FAD-dependent D-lactate dehydrogenase (dld) gene resulting in inactivation or reduction of its inherent activity, and
a disruption in said *Escherichia coli* of an endogenous pyruvate formate-lyase (pfl) gene resulting in inactivation or reduction of its inherent activity,
wherein said ldhA gene is integrated into an expression plasmid and said ldhA gene product is expressed under the control of an *Escherichia coli* strong promoter that is not a promoter of the ldhA gene, and wherein said genetically-engineered *Escherichia coli* produces at least 86.4 g/L D-lactic acid at 30 hours when cultured.

18. The genetically-engineered *Escherichia coli* of claim 17, wherein said promoter is a glyceraldehyde-3-phosphate dehydrogenase (GAPDH) promoter, and wherein said genetically-engineered *Escherichia coli* produces at least 115.6 g/L D-lactic acid at 48 hours.

* * * * *

SEQUENCE LISTING

<160> NUMBER OF SEQ ID NOS: 36

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggaattcgtc gaccggctcc agttcgaagc tggt         34

<210> SEQ ID NO 2
<211> LENGTH: 32
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 2
ggaattctga ctcagctaac aataaaattt tt                                        32

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggaattccgg agaaagtctt atgaaact                                             28

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccaagcttt taaaccagtt cgttcgggc                                            29

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcacgaaagc tttgattacg                                                      20

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttattgcatg cttagatttg actgaaatcg                                           30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttattgcatg cttatttact gcgtacttcg                                           30

<210> SEQ ID NO 8
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
aaggcctacg aaaagctgca g                                              21

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caacaccaag ctttcgcg                                                  18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttccactcct tgtggtggc                                                 19

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aactgcagaa attacggatg gcagag                                         26

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgttctagaa agttctttga c                                              21

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aacgaattct cgcaatgatt gacacgattc                                     30

<210> SEQ ID NO 14
<211> LENGTH: 32
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
acagaattcg ctatttgtta gtgaataaaa gg                                    32

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggaattccgg agaaagtctt atgaaact                                         28

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cccaagcttt taaaccagtt cgttcggggc                                       30

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaggtaccac cagagcgttc tcaagc                                           26

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gctctagatt ctccagtgat gttgaatcac                                       30

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggtctagagc aatgattcac acgattcg                                         28

<210> SEQ ID NO 20
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 20
aactgcaggt tcgttctcat acacgtcc                                            28

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaaggtacca gaataccttc tgctttgccc                                          30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaaggatccc ctaaactcct tattatattg                                          30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aaaggatcca aaccggagca cagactccgg                                          30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaatctagaa tcagatcatc gtcgccttac                                          30

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acggagcatg acggcaagc                                                      19

<210> SEQ ID NO 26
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 26
aatctagaca ccccatctta tcgtttg                                            27

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tttctagatc ttcctcttct gcaaaccc                                           28

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctttgagctc acgcgaggcc aggttatc                                           28

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agtgaattct cacagccagt gcgccga                                            27

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agtggatccc gcatcgccaa tgtaaatcc                                          29

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agtggatccg acattcctcc agattgtttt t                                       31

<210> SEQ ID NO 32
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 32
ataacgcaag aaagcttgtt ga                                             22

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttttgagctc gatcaggatt gcgttggtgg                                     30

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgaacagtaa tcgtacaggg                                                20

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tacgattact gttcggcatc gaccgaatac ccgag                               35

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tttttctaga cctggcacgc ctctcttctc                                     30
```